(12) United States Patent
Schwarz et al.

(10) Patent No.: US 7,838,699 B2
(45) Date of Patent: *Nov. 23, 2010

(54) EMBOLIZATION USING DEGRADABLE CROSSLINKED HYDROGELS

(75) Inventors: Alexander Schwarz, Brookline, MA (US); Hongmin Zhang, Duxbury, MA (US)

(73) Assignee: Biosphere Medical, Rockland, MA (US)

( * ) Notice: Subject to any disclaimer, the term of this patent is extended or adjusted under 35 U.S.C. 154(b) by 2356 days.

This patent is subject to a terminal disclaimer.

(21) Appl. No.: 10/389,708

(22) Filed: Mar. 14, 2003

(65) Prior Publication Data
US 2003/0215519 A1    Nov. 20, 2003

Related U.S. Application Data

(60) Provisional application No. 60/378,756, filed on May 8, 2002.

(51) Int. Cl.
*C07C 69/52* (2006.01)
*C07C 239/00* (2006.01)
*C08F 20/00* (2006.01)
*A61F 13/00* (2006.01)

(52) U.S. Cl. .................. 560/205; 560/312; 526/328; 424/422

(58) Field of Classification Search ................ None
See application file for complete search history.

(56) References Cited

U.S. PATENT DOCUMENTS

| 3,718,716 | A | 2/1973 | Joh et al. | 260/898 |
|---|---|---|---|---|
| 3,794,494 | A | 2/1974 | Kai et al. | 96/35.1 |
| 3,858,510 | A | 1/1975 | Kai et al. | 101/395 |
| 5,124,421 | A | 6/1992 | Ulbrich et al. | 526/212 |
| 5,130,479 | A | 7/1992 | Ulbrich et al. | 562/874 |
| 5,514,379 | A | 5/1996 | Weissleder et al. | 424/426 |
| 5,635,215 | A | 6/1997 | Boschetti et al. | 424/501 |
| 5,922,612 | A | 7/1999 | Alder et al. | 436/163 |
| 6,299,619 | B1 | 10/2001 | Green, Jr. et al. | 606/108 |
| 6,323,360 | B1 | 11/2001 | Ruckenstein et al. | 560/199 |
| 6,713,646 | B2 * | 3/2004 | Zhang et al. | 560/205 |
| 2001/0036451 | A1 | 11/2001 | Goupil et al. | 424/78.38 |
| 2001/0046518 | A1 | 11/2001 | Sawhney | 424/486 |

OTHER PUBLICATIONS

Argade et al.; "Preparation and Characterization of Novel Biodegradable Tri-and Tetraacrylate Intermediates", Polymer Bulletin 31: 401-407, (1993).
Bruining et al.; "Biodegradable Three-dimentional Networks of Poly(dimethylamino ethyl methacrylate). Synthesis, Characterization and in Vitro Studies of Structural Degradation and Cytotoxicity", Biomaterials 21:595-604, (2000).
Bruining et al.; "New Biodegradable Networks of Poly(N-Vinylpyrrolidinone)Designed for Controlled Nonburst Degradation in the Vitreous Body", J. Biomed. Mater. Res. 47: 189-197, (1999).
Eo Akala; "Hydrolysis of Linear Copolymers with Pendant N, O-Diacylhydroxylamine Moieties", Pharm. Pharmacol. Lett. 8, 3: 129-132, (1998).
Gombotz and Pettit; "Biodegradable Polymers for Protein and Peptide Drug Delivery", Bioconjugale Chem. 6: 332-351, (1995).
Grosse-Summer and Prud'homme; "Degradable Phosphazene-Crosslinked Hydrogels", Journal of Controlled Release, 40:261-267, (1996).
Ruckenstein and Zhang, "A Novel Breakable Cross-Linker and pH-Responsive Star-Shaped and Gel Polymers", Macromolecules 32: 3979-3983, (1999).
Sawhney et al.; "Bioerodible Hydrogels Based on Photopolymerized Poly(ethylene Glycol)-co-poly($\alpha$-hydroxy acid) Diacrylate Macromers", Macromolecules 26: 581-587, (1993).
Ulbrich et al.; "Novel Biodegradable Hydrogels Prepared Using the Divinylic Crosslinking Agent N,O-dimethacryloylhydroxylamine. 1. Synthesis and Characterization of Rates of Gel Degradation, and Rate of Release of Model Drugs, in Vitro and in Vivo", Journal of Controlled Release, 24: 181-190, (1993).
Ulbrich et al.; "Synthesis of Novel Hydrolytically Degradable Hydrogels for Controlled Drug Release", Journal of Controlled Release 34: 155-165, (1995).
International Search Report Completed on Jul. 25, 2003 and mailed on Aug. 18, 2003.

* cited by examiner

*Primary Examiner*—Robert A Wax
*Assistant Examiner*—Lyndsey Beckhardt
(74) *Attorney, Agent, or Firm*—Foley Hoag, LLP

(57) ABSTRACT

One aspect of the present invention relates to a method of temporarily embolizing a blood vessel using a hydrolytically degradable crosslinked hydrogel as an embolus. In certain embodiments, the hydrolytically degradable crosslinked hydrogel substantially hydrolyzes only at about physiological pH. In certain embodiments of the method, the hydrolytically degradable crosslinked hydrogel is stable at low pH. In certain embodiments of the method, the hydrolytically degradable crosslinked hydrogel comprises a marker molecule, such as a dye, radiopaque, or an MRI-visible compound. It is to be understood that both the foregoing general description and the following detailed description are exemplary, and are intended to provide further explanation of the invention as claimed.

63 Claims, 5 Drawing Sheets

EMBOLIZATION USING DEGRADABLE CROSSLINKED HYDROGELS

RELATED APPLICATIONS

This application claims the benefit of priority to U.S. Provisional Patent Application Ser. No. 60/378,756, filed May 8, 2002.

BACKGROUND OF THE INVENTION

Embolization is the selective blockage of one or more blood vessels supplying a diseased vascular structure or diseased tissue while simultaneously preserving the blood supply to surrounding normal vascular structure or tissue. For example, uterine fibroid embolization (UFE) is the process of occluding the vascular blood supply to uterine fibroids to reduce fibroid size and alleviate associated symptoms, including bleeding, pain, and disfigurement. Fibroids are benign tumors of smooth muscle. They are also called leiomyomas or myomas. Fibroids may arise in different parts of the uterus. They are named by their position within the uterus; submucosal, intramural, and subserosal. Some fibroids grow on a stalk and these are called pedunculated. Abnormal bleeding can be caused by submucosal or intramural fibroids. Intramural and subserosal fibroids can cause pelvic pain, back pain, and generalized pressure sensations. Fibroids often fail to respond to medical therapies, causing either myomectomy (surgical removal of the fibroids) or hysterectomy to be an ultimate treatment. In recent years, there has been considerable research aimed at developing less invasive alternatives to surgical treatments of fibroids. One such alternative is uterine fibroid embolization.

PCT/US99/04398 discloses a method for gynecological endovascular embolization with a fluid embolic composition that halicize forms a coherent solid mass. The embolization agent is a composition of biocompatible polymers and a radiopaque material. In some applications where a water soluble radiopaque material is used, the composition does not contain any particles. The particle size is no more than 100 micrometers and preferably less than 10 micrometers.

U.S. Pat. No. 4,999,188 (Solodovnik et al.) discloses a composition for embolization of blood vessels, in which agglomeration of particles is decreased as the composition is introduced. The proposed composition can additionally comprise a medicinal or radiopaque substance or a mixture of these in an amount of about 0.005 to about 8% by weight in relation to the total weight of the initial ingredients. The particles of the embolizing material may include particles of a polymer material moderately swelling in water, particles of glass or metal or a mixture thereof Suitable polymeric particles include acetylcellulose, acetylphtalylcellulose, polyvinylacetate, copolymers of vinylpyrrolidone and methylmethacrylate.

U.S. Pat. No. 5,202,352 (Okada et al.) discloses an intravascular embolizing agent containing an angiogenesis-inhibiting substance and an intravascular embolizing substance. The agent, with the administration of a relatively small dosage amount, enhances the anti-tumor effect of the angiogenesis-inhibiting substances. The addition of small doses of angiogenesis inhibiting substances also enhances the anti-tumor effect of intravascular embolizing agents.

U.S. Pat. No. 5,236,410 (Granov et al.) discloses a method for tumor treatment which involves first catheterization of the vessel that supplies a tumor of interest. A suspension of a magnetically hard ferromagnetic substance in an oil solution of oil-soluble antitumor agent is then injected through the catheter under fluoroscopic control and, at the same time, local magnetic field is applied onto the tumor-bearing area. After 1-3 days, the tumor is subjected to oscillating power field selected from ultrahigh radio frequency electromagnetic field and the field of ultrasonic contraction waves until the temperature of 43.0-43.5C. is reached within the tumor, and this temperature is maintained for 5-45 minutes. In cases of large size tumors it is preferable to reduce the blood flow in the tumor-feeding blood vessel after the administration thereto of the suspension.

U.S. Pat. No. 5,624,685 (Takahashi et al.) discloses a vascular lesion embolizing material comprising a high-polymer gel capable of absorbing water in an amount of 10 mL/g and more. When the high-polymer gel is supplied, either as such or after being bound with a binder or confined in a capsule, to the site of a blood vessel having a lesion to be repaired or its neighborhood, the gel swells upon contact with blood and spreads readily in the blood vessel to close the lumen of the blood vessels with lesion.

Still another approach to the embolization of an abnormal vascular site is the injection into the site of a biocompatible hydrogel, such as poly (2-hydroxyethyl methacrylate) ("pHEMA" or "PHEMA"); or a polyvinyl alcohol foam ("PAF"). See, e.g., Horak et al., "Hydrogels in Endovascular Embolization. II. Clinical Use of Spherical Particles", Biomaterials, Vol. 7, pp. 467-470 (November, 1986); Rao et al., "Hydrolysed Microspheres from Cross-Linked Polymethyl Methacrylate", J. Neuroradiol., Vol. 18, pp. 61-69 (1991); Latchaw et al., "Polyvinyl Foam Embolization of Vascular and Neoplastic Lesions of the Head, Neck, and Spine", Radiology, Vol. 131, pp. 669-679 (June, 1979). These materials are delivered as microparticles in a carrier fluid that is injected into the vascular site, a process that has proven difficult to control. A further development in this arena has been the formulation of hydrogel materials into a preformed implant or plug that is installed in the vascular site by means such as a microcatheter. See, e.g., U.S. Pat. Nos. 5,258,042—Mehta and 5,456,693—Conston et al. These types of plugs or implants are primarily designed for obstructing blood flow through a tubular vessel or the neck of an aneurysm, and they are not easily adapted for precise implantation within a sack-shaped vascular structure, such as an aneurysm, so as to fill substantially the entire volume of the structure.

As underscored by the preceding overview, the vast majority of the agents used today embolize permanently. However, there are numerous clinical situations, e.g., trauma, postpartum hemorrhage, and GI bleeding, in which temporary embolization is desired. The typical aim of temporary embolization is to block blood flow to the punctured site, allowing the blood vessel to heal over. As a temporary embolization agent degrades, the blood vessel recanalizes, reestablishing the old vasculature.

The temporary embolization agent used most frequently today in the clinical setting is gelfoam. This embolic agent comes in the form of sheets. Physicians cut sheet gelfoam into pieces, and inject them into a vessel through a catheter. Gelfoam is degraded by proteases in the blood stream. However, due to differences in enzyme expression from one patient to another, and variation in the size of the pieces of gelfoam used, the in vivo degradation times of this embolization agent span a wide range, i.e., from hours to weeks. Another temporary embolization agent that has been used clinically is starch microspheres. Starch microspheres degrade rapidly, i.e., within minutes to hours, due to the action of α-amylase; unfortunately, this timeframe is too short for most applications.

Autologous materials, e.g., fat, dura mater, muscle and autologous clot, have also been used for temporary embolization. The main advantage of these materials is their low cost and their inherent biocompatibility. The autologous agent used most frequently is autologous clot. There are several disadvantages associated with using this kind of embolic agent. As noted in connection with gelfoam, the degradation of autologous materials relies on enzymatic action. Because enzyme expression varies from person to person, the degradation time cannot be accurately predicted.

The use of hydrolytically degradable materials for embolization promises to provide a means to exercise control over the in vivo lifetime of an embolus. Importantly, enzyme activity would not be a factor in the degradation rate of the embolus. Further, the quantity and pH of the aqueous solution present at the site of embolization can be predicted accurately. Materials comprising hydrolytically degradable polymers have been used to prepare hydrolytically degradable emboli.

There are two archetypal ways to render a polymeric material hydrolytically degradable. The first way is to use hydrophobic linear polymers, such as poly(lactic acid/glycolic acid) (PLGA), polyanhydrides, polyesters, and polyesteramides, that degrade into soluble monomers and oligomers. For example, PLGA microspheres have been utilized for embolization. While the degradation time could be controlled in vitro, the minimum time for degradation is on the order of weeks. Further, the PLGA microspheres are rigid beads, which means that they cannot deform and regain their shape when pushed through a catheter with a smaller orifice than the diameter of the beads. Additionally, microspheres made of PLGA or other hydrophobic linear polymers degrade by surface erosion. Therefore, as the beads degrade, the diameter of the beads decreases, creating a possibility that the beads will simply get carried further into the vasculature.

A second way to render a polymeric material hydrolytically degradable is the use of crosslinked polymers comprising hydrolytically degradable crosslinks. For example, hydrolytically degrading polymers were synthesized in situ using photopolymerization of monomers in the presence of crosslinkers containing a hydrolytically unstable lactic acid moiety (Sawhney et al, Macromolecules, 26 (1993) 581-587). The degradation time of these polymers was a function of the number of lactic acid moieties incorporated into the crosslinker and the final polymer. Unfortunately, the lactic acid-containing crosslinker must be stored under anhydrous conditions due to its ready hydrolysis. Other crosslinkers have been prepared containing hydrolytically labile carbonate (Bruining et al, Biomaterials 21 (2000) 595-604), ester (Argade et al, Polymer Bulletin 31 (1993) 401-407, and phosphazene moieties (Grosse-Sommer et al, Journal of Controlled Release 40 (1996) 261-267). Hydrogels comprising such crosslinked polymers are not stable under the conditions described above, and start to degrade immediately following placement in an aqueous environment at any pH value.

A crosslinked polymeric material may also be rendered hydrolytically degradable by incorporating crosslinks which are stable under basic or acidic conditions, but which degrade at physiological pH. Ruckenstein et al (Macromolecules, 32 (1999) 3979-3983; U.S. Pat. No. 6,323,360) described a crosslinker, derived from ethylene glycol divinyl ether and methacrylic acid, with this degradation profile. The Ruckenstein et al crosslinker contains hemiacetal functions, accounting for its stability at high pH, and instability under acidic conditions. Likewise, Ulbrich et al (Journal of Controlled Release, 24 (1993)181-190; Ulbrich et al, Journal of Controlled Release, 34 (1995) 155-165; U.S. Pat. Nos. 5,130,479; and 5,124,421) have described a crosslinker, N,O-dimethacryloylhydroxylamine, that is stable only at low pH. The degradation of the Ulbrich et al crosslinker is postulated to occur via base-catalyzed Lossen rearrangement of substituted hydroxamic acids. Notably, none of these approaches has been utilized to prepare temporary embolic particles.

Degradable hydrogel beads that are compliant and resilient are expected to serve as effective emboli. Hydrogel beads of this type would be able to pass through an orifice with a diameter smaller than the diameter of the beads, thus enabling highly selective embolization. Moreover, through bulk degradation, their degradation times can be controlled because it will be only a function of the blood pH, and the number and type of crosslinks.

SUMMARY OF THE INVENTION

One aspect of the present invention relates to a method of temporarily embolizing a blood vessel using a hydrolytically degradable crosslinked hydrogel as an embolus. In certain embodiments, the hydrolytically degradable crosslinked hydrogel substantially hydrolyzes only at about physiological pH. In certain embodiments of the method, the hydrolytically degradable crosslinked hydrogel is stable at low pH. In certain embodiments of the method, the hydrolytically degradable crosslinked hydrogel comprises a marker molecule, such as a dye, radiopaque, or an MRI-visible compound. It is to be understood that both the foregoing general description and the following detailed description are exemplary, and are intended to provide further explanation of the invention as claimed.

DETAILED DESCRIPTION OF THE INVENTION

Figure 1:
FIG. 1 depicts angiograms of a kidney embolized with degradable polymeric microspheres according to a method of the present invention. See Example 23. The angiograms were obtained immediately following embolization and at one, two and three weeks subsequent to embolization, respectively.
Figure 1:
Figure 1:
Figure 1:
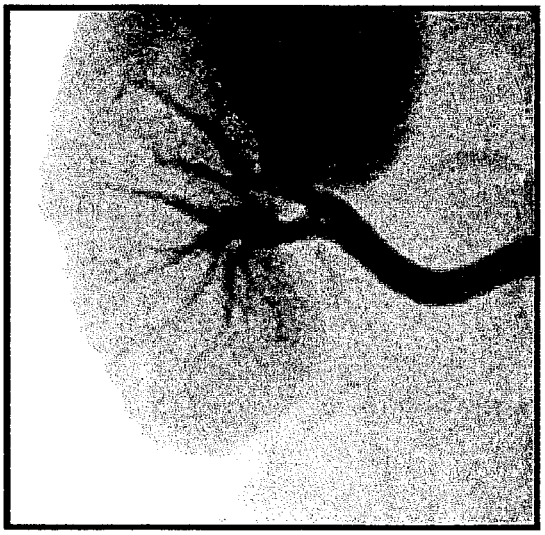

The invention will now be described more fully with reference to the accompanying examples, in which preferred embodiments of the invention are shown. This invention may, however, be embodied in many different forms and should not be construed as limited to the embodiments set forth herein;

rather, these embodiments are provided so that this disclosure will be thorough and complete, and will fully convey the scope of the invention to those skilled in the art.

One aspect of the present invention relates to a method of temporarily embolizing a blood vessel using a hydrolytically degradable crosslinked hydrogel as an embolus. In certain embodiments of the method, the hydrolytically degradable crosslinked hydrogel is stable at high pH. In certain embodiments of the method, the hydrolytically degradable crosslinked hydrogel is stable at low pH. In certain embodiments of the method, the hydrolytically degradable crosslinked hydrogel comprises a marker molecule, such as a dye, radiopaque, or an MRI-visible compound.

Embolization

Embolization is a process wherein a material is injected into a blood vessel to at least partially fill or plug the blood vessel and/or encourage clot formation so that blood flow through the vessel is reduced or stopped (See also Background of the Invention). Embolization of a blood vessel can be useful for a variety of medical reasons, including preventing or controlling bleeding due to lesions (e.g., organ bleeding, gastrointestinal bleeding, vascular bleeding, and bleeding associated with an aneurysm), or to ablate diseased tissue (e.g., tumors, vascular malformations, hemorragic processes, etc.) by cutting off blood supply. Embolization may also be used to prevent blood loss during or immediately following surgery. Embolization of tumors may be performed preoperatively to shrink tumor size; to aid in the visualization of a tumor; and to minimize or prevent blood loss related to surgical procedures.

In other words, embolization is useful in a broad spectrum of clinical situations. Embolization can be particularly effective in hemorrhage, regardless of whether the etiology is trauma, tumor, epistaxis, postoperative hemorrhage, or GI hemorrhage. It can be performed anywhere in the body that a catheter can be placed, including the intracranial vasculature, head and neck, thorax, abdomen, pelvis, and extremities. With the availability of coaxial microcatheters, highly selective embolizations can be performed. In most patients, embolization for hemorrhage is preferable to surgical alternatives.

Emobilization may be used in treating skin, head, or neck tumors, tumors of the uterus or fallopian tubes, liver or kidney tumors, endometriosis, fibroids, etc. Particularly, embolization has been used for arteriovenous malformation of the pelvis, kidney, liver, spine and brain. Uterine artery embolization has been used for the treatment of fibroids; renal artery embolization has been used for the treatment of renal angiomyolipomas and renal cell carcinoma; intracranial embolization has been used for the treatment of cerebral and intracranial aneurysms, neuroendocrine metastases, intracranial dural arteriovenous fistula and patent ductus arteriosus. Other examples of specific embolization procedures include hepatic artery embolization and pulmonary artery embolization. Examples of such procedures are described, e.g., in Mourikis D., Chatziioannou A., Antoniou A., Kehagias D., Gikas D., Vlahous L., "Selective Arterial Embolization in the Management of Symptomatic Renal Angiomyolipomas (AMLs)," European Journal of Radiology 32(3):153-9, 1999 Dec.; Kalman D. Varenhorst E., "The Role of Arterial Embolization in Renal Cell Carcinoma," Scandinavian Journal of Urology & Nephrology, 33(3):162-70, 1999 Jun.; Lee W., Kim T S., Chung J W., Han J K., Kim S H., Park J H., "Renal Angiomyolipoma: Embolotherapy with a Mixture of Alcohol and Iodized Oil," Journal of Vascular & Interventional Radiology, 9(2):255-61, 1998 March-April; Layelle I., Flandroy P., Trotteur G., Dondelinger R F., "Arterial Embolization of Bone Metastases: is it Worthwhile?" Journal Belge de Radiologie, 81(5):223Oct. 5, 1998; Berman, M F., Hartmann A., Mast H., Sciacca R R., Mohr J P., PileSpellman J., Young W L., "Determinants of Resource Utilization in the Treatment of Brain Arteriovenous Malformations," Ajnr: American Journal of Neuroradiology, 20(10):2004-Nov.-Dec. 8, 1999 ; Shi H B., Suh D C., Lee H K., Lim S M., Kim D H., Choi C G., Lee C S., Rhim S C., "Preoperative Transarterial Embolization of Spinal Tumor: Embolization Techniques and Results," Ajnr: American Journal of Neuroradiology, 20(10):2009-Nov-Dec.15, 1999 ; Nagino M., Kamiya J., Kanai M., Uesaka K., Sano T., Yamamoto H., Hayakawa N., Nimura Y., "Right Trisegment Portal Vein Embolization for Biliary Tract Carcinoma: Technique and Clinical Utility," Surgery, 127(2):155-60,Feb. 2000; Mitsuzaki K., Yamashita Y., Utsunomiva D., Sumi S., Ogata I., Takahashi M., Kawakami S., Ueda S., "Balloon-Occluded Retrograde Transvenous Embolization of a Pelvic Arteriovenous Malformation," Cardiovascular & Interventional Radiology 22(6):518-Nov-Dec. 20, 1999.

In many instances, embolization procedures begin with diagnostic angiography to identify the source of bleeding. For example, in epistaxis, angiography of the external carotid artery with attention to the internal maxillary artery can be helpful. In pelvic fractures, the internal iliac arteries are examined angiographically. Selective and superselective angiography is more sensitive in finding the source of bleeding than are nonselective studies. Consequently, clinical suspicion and the results of other imaging studies, such as contrast-enhanced CT and radionuclide scans with Technetium Tc 99m-labeled RBCs, are important in guiding angiographic examination. In intra-abdominal bleeding, such as after complex trauma, CT scan may identify the site of acute bleeding, because acute bleeding often demonstrates higher density (Hounsfield units) than older blood; this is termed the "sentinel clot sign."

Hemorrhage may be identified by active extravasation of contrast outside of the confines of the vessel lumen. The angiographic appearance depends on the rate and location of bleeding. The extravasating contrast medium may flow towards the dependent part of the viscus; in the bowel, the extravasated contrast may outline the mucosa. When the bleeding site and artery have been identified on the initial angiogram, a catheter, often a 3F microcatheter, is placed as selectively as possible into the bleeding artery to confirm the bleeding and to stop it with embolization.

Coils have historically been the agent of choice for embolization. Coils are available in a variety of shapes and sizes; the largest coils measure 15 mm in diameter when deployed. Such a coil would be large enough to fill the common iliac artery, for instance. Once microcatheter technology (3F or smaller) became available, microcoils were developed to embolize increasingly smaller vessels. Microcoils assume a deployment diameter as small as 1 mm. In addition, some coils are straight when deployed; thus, the coil has the same diameter as the wire from which it is made (the term "straight coil" is a misnomer). The advantages of coils include their high radiopacity and that they can be deployed with high accuracy.

Particulate embolic agents are also useful in embolization. For example, acute hemorrhage may be treated using particulate embolic agents, including those comprised of polyvinyl alcohol (PVA), Embosphere Microsphere™ (see U.S. Pat. Nos. 5,648,100; and 5,635,215), and an absorbable gelatin sponge (Gelfoam). These agents are mixed with an iodine-contrast agent for fluoroscopic visualization and injected through a catheter or microcatheter. PVA is available in particle sizes ranging from 50-2000 micrometers, while Embospheres are available in particle sizes from 40-1200 micrometers. An appropriate range of particle size must be chosen based on the size of the vessels to be occluded. The smaller the particles, the more distal the embolization, and the greater the likelihood of tissue necrosis.

As noted above, gelfoam has also been used as a temporary occlusive agent; however, it can incite an inflammatory response, contributing to permanent thrombosis. Once injected, gelfoam induces a thrombogenic reaction, occluding the vessel. However, once occluded, thrombolytic enzymes degrade the clot and gelfoam, recanalizing the occluded vessel over a period of days to weeks. Gelfoam can be useful in trauma where a temporary occlusion is desired while either surgical repair of the injury is undertaken or the body's natural healing processes repair the damage. Gelfoam is available as either a sponge, which can be cut into pieces or from which a slurry can be made, or as powdered particles that average approximately 50 micrometers in diameter.

An embolizing agent is usually delivered using a catheter. The catheter delivering the embolizing agent composition may be a small diameter medical catheter. The particular catheter employed is not critical, provided that the catheter components and the embolizing agent are mutually compatible. In this regard, polyethylene catheter components can be useful. Other materials compatible with the embolizing agent composition may include fluoropolymers and silicone.

Once a catheter is in place, an embolizing agent composition containing microparticles is injected through the catheter slowly, typically with the assistance of X-ray or flouroscopic guidance. The particles should be of sufficient size that they do not remain mobile in the body. If the particles are too small, they can be engulfed by the body's white blood cells and carried to distant organs or be carried away in the microvasculature and travel until they reach a site of greater constriction. In preferred embodiments of the methods of the present invention, the embolic microparticies have a transverse cross-sectional dimension between 50 and 3,000 micrometers.

The embolizing agent composition can be introduced directly into critical blood vessels or they may be introduced upstream of target vessels. The amount of embolizing microparticles introduced during an embolization procedure will be an amount sufficient to cause embolization, e.g., to reduce or stop blood flow through the target vessels. The amount of embolizing agent composition delivered can vary depending on, e.g., the total of the vasculature to be embolized, and the concentration and size of the microparticles. Adjustment of such factors is within the skill of the ordinary artisan in the embolizing art.

After embolization, another arteriogram may be performed to confirm the completion of the procedure. Arterial flow will still be present to some extent to healthy body tissue proximal to the embolization, while flow to the diseased or targeted tissue is blocked. The procedure can take approximately 1 to 1 ½ hours. As a result of the restricted blood flow, the diseased or targeted tissue begins to shrink.

Selected Clinical Applications of Embolization

As discussed above, embolization typically is performed using angiographic techniques with guidance and monitoring, e.g., fluoroscopic or X-ray guidance, to deliver an embolizing agent to vessels or arteries. Further, a vasodilator (e.g., adenosine) may be administered to the patient beforehand, simultaneously, or subsequently, to facilitate the procedure.

Importantly, while portions of the subsequent description include language relating to specific clinical applications of embolization, all types of embolization processes are considered to be within the contemplation of the methods of the present invention. Specifically, one of skill in the medical or embolizing art will understand and appreciate how microparticles of hydrolytically degradable hydrogels as described herein can be used in various embolization processes by guiding a delivery mechanism to a desired vascular body site, and delivering an amount of the microparticles to the site, to cause restriction, occlusion, filling, or plugging of one or more desired vessels and reduction or stoppage of blood flow through the vessels. Factors that might be considered, controlled, or adjusted for, in applying the process to any particular embolization process might include the chosen composition of the microparticles (e.g., to account for imaging, tracking, and detection of a radiopaque particle substrate); the amount of microparticles delivered to the body site; the method of delivery, including the particular equipment (e.g., catheter) used and the method and route used to place the dispensing end of the catheter at the desired body site, etc. Each of these factors will be appreciated by one of ordinary skill, and can be readily dealt with to apply the described methods to innumerable embolization processes.

A. Head and Neck

In the head and neck, embolotherapy most often is performed for epistaxis and traumatic hemorrhage. Otorhinolaryngologists differentiate anterior and posterior epistaxis on anatomic and clinical bases. Epistaxis results from a number of causes, including environmental factors such as temperature and humidity, infection, allergies, trauma, tumors, and chemical irritants. An advantage of embolization over surgical ligation is the more selective blockade of smaller branches. By embolizing just the bleeding branch, normal blood flow to the remainder of the internal maxillary distribution is retained. Complications of embolization may include the reflux of embolization material outside the intended area of embolization, which, in the worst case, may result in stroke or blindness. Embolization has been proven more effective than arterial ligation. Although embolization has a higher rate of minor complications, no difference in the rate of major complications was found. For traumatic hemorrhage, the technique of embolization is the same as for epistaxis. Because of the size of the arteries in the head and neck, microcatheters are often required.

B. Thorax

In the thorax, the two main indications for embolization in relation to hemorrhage are: (1) pulmonary arteriovenous malformations (PAVM); and (2) hemoptysis. PAVMs usually are congenital lesions, although they may occur after surgery or trauma. The congenital form is typically associated with hereditary hemorrhagic telangiectasia, also termed Rendu-Osler-Weber syndrome. There is a genetic predisposition to this condition. PAVMs can be single or multiple, and if large enough, can result in a physiologic right-to-left cardiac shunt. Clinical manifestations of the shunt include cyanosis and polycythemia. Stroke and brain abscesses can result from paradoxical embolism. PAVMs also may hemorrhage, which results in hemoptysis.

Treatment options for PAVMs include surgery and transcatheter therapy. The treatment objective is to relieve the symptoms of dyspnea and fatigue associated with the right-to-left shunt. In addition, if the patient suffers from paradoxical embolism, treatment prevents further episodes. As a result of the less invasive nature of the procedure and excellent technical success rate, embolization currently is considered the treatment of choice for PAVM, whether single or multiple. Embolotherapy is the clear treatment of choice for PAVMs.

Bronchial artery embolization is performed in patients with massive hemoptysis, defined as 500 cm³ of hemoptysis within a 24-hour period. Etiologies vary and include bronchiectasis, cystic fibrosis, neoplasm, sarcoidosis, tuberculosis, and other infections. Untreated, massive hemoptysis carries a high mortality rate. Death most often results from asphyxiation rather than exsanguination. Medical and surgical treatments for massive hemoptysis usually are ineffective, with mortality rates ranging from 35-100%. Embolization has an initial success rate of 95%, with less morbidity and mortality than surgical resection. Consequently, transcatheter embolization has become the therapy of choice for massive hemoptysis, with surgical resection currently reserved for failed embolization or for recurrent massive hemoptysis following multiple prior embolizations.

C. Abdomen and Pelvis

Many indications for embolization in the abdomen and pelvis exist. For embolization of hemorrhage, the most common indication is acute GI hemorrhage. Solid organ injury, usually to the liver and spleen, can readily be treated with embolization. Other indications exist, such as gynecologic/obstetric-related hemorrhage and pelvic ring fractures.

Once the source of bleeding is identified, an appropriate embolization procedure can be planned. The technique for embolization is different for upper GI bleeding and lower GI bleeding. The vascular supply in the UGI tract is so richly collateralized that relatively nonselective embolizations can be performed without risk of infarcting the underlying organs. Conversely, the LGI tract has less collateral supply, which necessitates more selective embolizations.

Outside the GI tract, there are organ specific considerations when performing embolizations in the abdomen. For instance, the liver has a dual blood supply, with 75% of the total supply from the portal vein and 25% from the hepatic artery. The hepatic artery invariably is responsible for hemorrhage resulting from trauma due to its higher blood pressure compared to the portal vein. Therefore, all embolizations in the liver are performed in the hepatic artery and not in the portal vein. Because of the dual blood supply, occlusion of large branches of the hepatic artery can be performed without risk of necrosis.

In contrast, embolizations of the spleen always should be performed as distally as possible. Occlusion of the splenic artery can result in splenic necrosis and the possibility of a splenic abscess postembolization. If occlusion of the entire splenic artery is contemplated for traumatic hemorrhage, total splenectomy instead of embolization or total splenectomy postembolization should be performed.

Further indications for hemorrhage embolization in the abdomen and pelvis include postpartum, postcesarean, and postoperative bleeding. Differential diagnoses for postpartum bleeding include laceration of the vaginal wall, abnormal placentation, retained products of conception, and uterine rupture. Conservative measures for treating postpartum bleeding include vaginal packing, dilatation and curettage to remove retained products, IV and intramuscular medications (eg, oxytocin, prostaglandins), and uterine massage. When conservative methods fail, embolization is a safe and effective procedure for controlling pelvic hemorrhage, avoids surgical risks, preserves fertility, and shortens hospital stays.

Finally, embolization of the internal iliac arteries is valuable in patients with hemodynamically unstable pelvic fractures. Protocols for trauma include treatment of associated soft-tissue injury first, followed by stabilization of the pelvic ring. Patients with persistent hemodynamic instability are candidates for embolization. As in other clinical settings, angiography is used to identify the source of hemorrhage, and a selective embolization is performed.

Embolizing Agent Compositions

According to the invention, the embolizing agent composition comprises a combination of microparticles and a biocompatible carrier. In certain embodiments, the embolizing agent composition is injectable. The embolizing agent composition can preferably comprise a contrast-enhancing agent which can be tracked and monitored by known methods, including radiography and fluoroscopy. The contrast-enhancing agent can be any material capable of enhancing contrast in a desired imaging modality (e.g., magnetic resonance, X-ray (e.g., CT), ultrasound, magnetotomography, electrical impedance imaging, light imaging (e.g. confocal microscopy and fluorescence imaging) and nuclear imaging (e.g. scintigraphy, SPECT and PET)), and is preferably capable of being substantially immobilized within the particles, e.g., included in the microparticles as part of a carbon coating or as part of a particle substrate. Contrast-enhancing agents are well known in the arts of embolization and similar medical practices, with any of a variety of such contrast-enhancing agents being suitable for use according to the methods of the invention.

Preferred embodiments of the invention can include a contrast-enhancing agent that is radiopaque in nature, in particular, a radiopaque material which exhibits permanent radiopacity, as many metals or metal oxides do. Permanent radiopacity is unlike some other contrast-enhancing agents or radiopaque materials used in embolization or similar medical applications which biodegrade or otherwise lose their effectiveness (radiopacity) over a certain period, e.g., days or weeks, such as 7 to 14 days. (See, e.g., PCT/GB98/02621). Advantage is that permanent radiopaque materials can be monitored or tracked for as long as they remain in the body, whereas other non-permanent contrast-enhancing agents or radiopaque materials have a limited time during which they may be detected and tracked.

The contrast-enhancing agent may be incorporated into the microparticle as part of the particle substrate. In one sense, a contrast-enhancing agent can be added to a material that is not detectable, e.g., not radiopaque, to make that material detectable. The contrast-enhancing agent may be provided in any such portion of a microparticle by known methods. According to a preferred mode of the invention, a permanent radiopaque material, such as a metal or metal oxide, can be incorporated into a hydrolytically degradable crosslinked hydrogel. The particle substrates themselves are permanently radiopaque, and can be individually and permanently detected and tracked following deposition into the body.

Some examples of radiopaque materials include paramagnetic materials (e.g. persistent free radicals or more preferably compounds, salts, and complexes of paramagnetic metal species, for example transition metal or lanthanide ions); heavy atom (i.e. atomic number of 37 or more) compounds, salts, or complexes (e.g. heavy metal compounds, iodinated compounds, etc.); radionuclide-containing compounds, salts, or complexes (e.g. salts, compounds or complexes of radioactive metal isotopes or radiodinated organic compounds); and superparamagentic particles (e.g. metal oxide or mixed oxide particles, particularly iron oxides). Preferred paramagnetic metals include Gd (III), Dy (III), Fe (II), Fe (III), Mn (III) and Ho (III), and paramagnetic Ni, Co and Eu species. Preferred heavy metals include Pb, Ba, Ag, Au, W, Cu, Bi and lanthanides such as Gd, etc.

The amount of contrast-enhancing agent included in a microparticle should be sufficient to allow detection of the microparticle as desired. Preferably, microparticles of the embolizing agent composition can comprise from about 10 to about 50 weight percent of contrast-enhancing agent, more preferably from about 20 to 40 weight percent contrastenhancing agent, and even more preferably about 30 weight percent contrast-enhancing agent. Optionally, some, i.e., only a portion, but not all microparticles used in a particular embolization procedure can include a contrast-enhancing agent. Microparticles that include a permanent radiopaque particle substrate can preferably have greater than 50 percent of their mass made up of the particle substrate.

As stated, the carrier can be any biocompatible fluid capable of delivering the microparticles to a desired site. Examples of suitable materials for a carrier can include saline, dextran, glycerol, polyethylene glycol, corn oil or safflower, or other polysaccharides or biocompatible organic polymers either singly or in combination. In use, the embolic agent composition can typically be injected in a fluid state, e.g., as a slurry, fluid suspension or emulsion, or as a gel, through a catheter, syringe needle, or cannula into a body site. When deposited into the blood stream, the carrier will disperse or be destroyed.

Hydrogels

As is known in the art, a hydrogel is a polymeric network formed by crosslinking one or more multifunctional backbone molecules or polymers. The resulting polymeric network is hydrophilic and swells in an aqueous environment thus forming a gel-like material, i.e., a hydrogel. Typically, a hydrogel comprises a backbone bonded to a crosslinking agent.

Hydrogels are characterized by their water-insolubility, hydrophilicity, high-water absorbability and swellable properties. The molecular components, units or segments of a hydrogel are characterized by a significant portion of hydrophilic components, units or segments, such as segments having ionic species or dissociable species, such as acids (e.g., carboxylic acids, phosphonic acids, sulfonic acids, sulfinic acids, phosphinic acids, etc.), bases (e.g., amine groups, proton accepting groups), or other groups that develop ionic properties when immersed in water (e.g., sulfonamides). Acryloyl groups (and to a lesser degree methacryloyl groups) and the class of acrylic polymers, polymer chains containing or terminated with oxyalkylene units (such as polyoxyethylene chains or polyoxyethylene/polyoxypropylene copolymer chains) are also well recognized as hydrophilic segments that may be present within hydrophilic polymers Certain preferred water insoluble polymeric compositions useful in the present invention are listed below, although the entire class of hydrogel materials known in the art may be used to varying degrees. The polymers set forth below and containing acid groups can be, as an option, partially or completely neutralized with alkali metal bases, either in the monomer or the polymer or both. While the list below contains many of the preferred polymers which may be used in hydrogels, the present invention is not limited to the use of just these polymers. Generally, polymers traditionally understood as hydrogels by those skilled in the art can also be used; for example: a) polyacrylic acid, polymethacrylic acid, polymaleic acid, copolymers thereof, and alkali metal and ammonium salts thereof; b) graft copolymers of starch and acrylic acid, starch and saponified acrylonitrile, starch and saponified ethyl acrylate, and acrylate-vinyl acetate copolymers saponified; c) polyvinyl alcohol, polyvinylpyrrolidone, polyvinyl alkylether, polyethylene oxide, polyacrylamide, and copolymers thereof; d) copolymers of maleic anhydride and alkyl vinylethers; and e) saponified starch graft copolymers of acrylonitrile, acrylate esters, vinyl acetate, and starch graft copolymers of acrylic acid, methylacrylic acid, and maleic acid.

The above exemplary polymers are cross-linked either during polymerization or after the core is encapsulated. This cross-linking is achieved using hydrolytically degradable cross-linking agents by methods known to those skilled in the art. This cross-linking can be initiated in the presence of radiation or a chemical free radical initiator.

One of the many useful properties of hydrogels is their ability to absorb water and swell without dissolution of the matrix. As a hydrogel swells, the pore size of the hydrogel increases, enhancing uptake of aqueous solutions and the diffusion of entrapped compounds out of the hydrogel. These properties have allowed use of hydrogels as controlled drug release systems and as absorbent materials. However, the rate of swelling of dried hydrogels upon exposure to an aqueous solution is limited by diffusion of water into the glassy polymer matrix. Conventional dried hydrogels have relatively small pore sizes resulting in slow swelling and release or absorption of liquids. The size of the pores in the hydrogel can be a factor used in the selection of hydrogels with the appropriate properties for the specific vessel to be embolized in the practice of the present invention. The larger the pore size, the generally higher rate of initial swelling a hydrogel undergoes.

Among the many hydrogel polymers which are useful as matrix polymers include poly(hydroxyalkyl methacrylate)s of which poly-(2-hydroxyethyl methacrylate), poly(glyceryl methacrylate) and poly(hydroxypropyl methacrylate) are well-known and identified in the literature as (P-HEMA), (P-GMA) and (P-(HPMA), respectively. Other hydrogel polymers include poly(acrylamide), poly(methacrylamide), poly(N-vinyl-2-pyrrolidine), and poly(vinyl alcohol), hydroxypropyl guar, high molecular weight polypropylene glycol or polyethylene glycol, and the like.

Non-limiting examples of the unsaturated monomers used as a starting material include those polymerizable monomers known to be soluble in water, water/organic mixtures and organic solvents. Examples of these unsaturated monomer are: monomers containing an acid group, such as acrylic acid, beta-acryloyloxypropionic acid, methacrylic acid, crotonic acid, maleic acid, maleic anhydride, fumaric acid, itaconic acid, cinnamic acid, sorbic acid, 2-(meth)acryloylethane sulfonic acid, 2-(meth)acryloylpropane sulfonic acid, 2-(meth) acrylamido-2-methylpropane sulfonic acid, vinyl sulfonic acid, styrene sulfonic acid, allyl sulfonic acid, vinyl phosphonic acid and 2-(meth)acryloyloxyethyl phosphate, and alkaline metal salts and alkaline earth metal salts, ammonium salts, and alkyl amine salts thereof; dialkyl amino alkyl(meth) acrylates, such as N,N-dimethylaminoethyl(meth)acrylate and N,N-dimethylaminopropyl(meth)acrylate, and quaternary compounds thereof (for example, a reaction product produced with alkylhalide, and a reaction product produced with dialkyl sulfuric acid); dialkyl amino hydroxyalkyl (meth)acrylates, and quaternary compounds thereof; N-alkyl vinyl pyridine halide; hydroxyalkyl(meth)acrylates, such as hydroxymethyl (meth)acrylate, 2-hydroxyethyl(meth)acrylate, and 2-hydroxypropyl (meth)acrylate; acrylamide, methacrylamide, N-ethyl (meth)acrylamide, N-propyl(meth)acrylamide, N-isopropyl(meth)acrylamide, N,N-dimethyl (meth) acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloyl piperidine, and N-acryloyl pyrrolidine; vinyl acetate; and alkyl (meth)

acrylates, such as methyl (meth)acrylate, and ethyl (meth) acrylate. These monomers may be used individually, or in combination.

Among the aforementioned monomers, unsaturated monomers containing an acrylate moiety are preferred because the resulting water-absorbent resins have significantly improved water absorption characteristics. Preferred acrylate monomers include acrylic acids and water-soluble salts of acrylic acids. The water-soluble salts of acrylic acids include alkaline metal salts, alkaline earth metal salts, ammonium salts, hydroxy ammonium salts, amine salts and alkyl amine salts of acrylic acids having a neutralization rate within a range of from 30 mol % to 100 mol %, more preferably within a range of from 50 mol % to 99 mol %. Among the exemplified water-soluble salts, sodium salt and potassium salt are more preferred. These acrylate monomers may be used individually or in combination. When the unsaturated monomer contains an acrylate moiety as a chief constituent, the amount of monomers other than the acrylate monomer is preferably less than 40 weight percent, more preferably less than 30 weight percent, and most preferably less than 10 weight percent of the total hydrogel. By using monomers other than the acrylate monomer in the above-mentioned ratios, the water absorption characteristics of the resulting water-absorbent resin are further improved.

The backbones of the hydrogels used in the methods of the present invention are prepared from a mixture comprising a monomer, which has an active group available to react with the terminal reactive moieties of the hydrolytically degradable crosslinking agent to form covalent linkages. Moreover, the degradation products should also be substantially biocompatible as defined below. By "biocompatible" it is intended that the monomer used in the backbone will not substantially adversely affect the body and tissue of the living subject into which the embolic hydrogel is to be injected. More particularly, the material does not substantially adversely affect the growth and any other desired characteristics of the tissue surrounding the implanted embolus. It is also intended that the material used does not cause any substantially medically undesirable effect in any other parts of the living subject. Methods for assessing the biocompatibility of a material are well known.

Examples of hydrogel backbones suitable for use in the microparticles used in the methods of embolization of the present invention include, but are not limited to, optionally substituted poly(acrylamide), optionally substituted poly (acrylate), proteins, glycoproteins, phosphorylated proteins, acylated proteins, and chemically modified proteins, peptides, aminocarbohydrates, glycosaminoglycans, aminolipids, polyols, polythiols, polycarboxylic acids, polyamines, such as dilysine, poly(vinylamine) and polylysine, poly(ethylene glycol) amines, and pharmaceutical agents having at least two active groups. Preferred examples of a suitable backbone include, but are not limited to, poly(N-substituted acrylamide), poly(acrylamide), and poly(acrylate). The hydrolytically degradable crosslinking agent used in the hydrogels may be in a linear, branched or star form. In branched or star forms, three or more linear polymers are covalently crosslinked.

As will be apparent, because of the hydrolytically degradable linkages incorporated in the crosslinking agent, the hydrogels used in the methods of the present invention are hydrolytically degradable. Thus, the hydrogels used in the embolization methods of the present invention gradually break down or degrade in the body due to the hydrolysis of the hydrolytically degradable crosslinks. The degradation or breakdown of the embolic hydrogels in the body is gradual in nature and subject to control due to the hydrolytically degradable crosslinkers. The ability to control the rate of hydrolytic degradation of the embolic hydrogels turns on the composition of the polymeric backbone, the type of crosslinker use, and the number of crosslinks in a particular embolus.

Embolic Microparticles

Microspheres have been manufactured and used in vivo to occlude blood vessels in the treatment of arteriovascular malformation, fistulas and tumors (See U.S. Pat. No. 5,635,215; and Laurent et al., J. Am. Soc. Neuroiol, 17:533-540 (1996); and Beaujeux et al. J. Am. Soc. Neuroial, A:533-540 (1996)).

In general, microparticles for use in the present invention may have any shape, with microparticles which are spherical in shape being preferred. Microparticles for use in the present invention may have diameters ranging between about 10 μm to about 5000 μm. Preferably, microparticles for use in the present invention will have diameters ranging between 50 μm and 3000 μm. The microparticles for use in the present invention are flexible, such that they can easily pass into and through injection devices and small catheters without being permanently altered.

The microparticles for use in the present invention are also stable in suspension which allows the microparticles to be formulated and stored in suspension and injected with different liquids. More specifically, the hydrophilic nature of the microparticles permits placing them in suspension, and in particular, in the form of sterile and pyrogenic (pyrogen-free) injectable solutions, while avoiding the formation of aggregates or adhesion to the walls of storage containers and implantation devices, such as catheters, syringes, needles, and the like. Preferably, these injectable solutions contain microparticles distributed approximately in caliber segments ranging between about 10 μm and about 5000 μm.

Microparticles may be prepared by suspension polymerization, drop-by-drop polymerization or any other method known to the skilled artisan. The mode of microparticle preparation selected will usually depend upon the desired characteristics, such as microparticle diameter and chemical composition, for the resulting microparticles. The microparticles of the present invention can be made by standard methods of polymerization described in the art (See, e.g., E. Boschetti, Microspheres for Biochromatography and Biomedical Applications. Part I, Preparation of Microbands In: Microspheres, Microencapsulation and Liposomes, John Wiley & Sons, Arshady R., Ed., 1998, which is incorporated herein by reference). The microspheres of the invention may also be obtained by other methods of polymerization, such as those described in French Patent 2,378,808 and U.S. Pat. No. 5,648,100, each of which is incorporated herein by reference. In general, the polymerization of monomers in solution is carried out at a temperature ranging between about 0° C. and about 100° C., and between about 40° C. and about 60° C., in th presence of a polymerization reaction initiator.

Polymerization can be carried out in mass or in emulsion. In the case of a mass polymerization, the aqueous solution containing the different dissolved constituents and the initiator undergoes polymerization in an homogeneous medium. This makes it possible to access a lump of aqueous gel which can then be separated into microspheres, by passing, for example, through the mesh of a screen. Emulsion or suspension polymerization is a preferred method of preparation, since it makes it possible to access directly microspheres of a desired size. It can be conducted as follows: The aqueous solution containing the dissolved constituents (e.g., different monomers), is mixed by stirring, with a liquid organic phase which is not miscible in water, and optionally in the presence of an emulsifier. The rate of stirring is adjusted so as to obtain an aqueous phase emulsion in the organic phase forming drops of desired diameter. Polymerization is then started off by addition of the initiator. It is accompanied by an exothermic reaction and its development can then be followed by measuring the temperature of the reaction medium. It is possible to use as the organic phase vegetable or mineral oils, certain petroleum distillation products, chlorinated hydrocarbons or a mixture of these different solutions. Furthermore, when the polymerization initiator includes several components (redox system), it is possible to add one of them in the aqueous phase before emulsification. The microspheres thus obtained can then be recovered by cooling, decanting and filtration. They are then separated by size category and washed to eliminate any trace of secondary product.

Injected microparticles can generate some transient adverse reactions, such as local inflammation; therefore, the microparticles may contain or be injected with anti-inflammatory drugs, such as: salicylic acid derivatives including aspirin; para-aminophenol derivatives including acetaminophen; non-steroidal anti-inflammatory agents including indomethacin, sulindac, etodolac, tolmetin, diclodfenac, ketorolac, ibuprofen, naproxen, flurbiprofen, ketoprofen, fenoprofen, oxaprozin; anthranilic acids including mefenamic acid, meclofenamic acid; enolic acids such as piroxicam, tenoxicam, phenylbutazone, oxyphenthatrarone; and nabumetone. These anti-inflammatories are preferably adsorbed in the microparticle's network and released slowly over a relatively short period of time (e.g., a few days). The microparticles may also be used to release other specific drugs which can be incorporated within the microparticle network before injection into the patient. The drug may be released locally at the site of implantation over a short period of time to improve the overall treatment.

Incorporation of active molecules, such as drugs, into the microparticles of the present invention can be accomplished by mixing dry microparticles with solutions of said active molecules or drugs in an aqueous or hydro-organic solution. The microparticles swell by adsorbing the solutions and incorporate the active molecule of interest into the microparticle network. The active molecules will remain inside the microparticle due to an active mechanism of adsorption essentially based on ion exchange effect. The ability of various types of microparticles to adsorb drug molecules may be readily determined by the skilled artisan, and is dependent on the monomers present in the initial solution from which the microparticles are prepared.

Embolization Kits

The methods of the present invention may also be practiced using an embolization kit comprising a degradable crosslinked hydrogel microparticle. Such kits may contain the degradable crosslinked hydrogel microparticle in sterile lyophilized form, and may include a sterile container of an acceptable reconstitution liquid. Suitable reconstitution liquids are disclosed in Remington's Pharmaceutical Sciences and The United States Pharmacopia—The National Formulary. Such kits may alternatively contain a sterile container of a composition of the degradable crosslinked hydrogel microparticle of the invention. Such kits may also include, if desired, other conventional kit components, such as, for example, one or more carriers, one or more additional vials for mixing. Instructions, either as inserts or labels, indicating quantities of the degradable crosslinked hydrogel microparticles and carrier, guidelines for mixing these components, and protocols for administration may also be included in the kit. Sterilization of the containers and any materials included in the kit and lyophilization (also referred to as freeze-drying) of the degradable crosslinked hydrogel microparticles may be carried out using conventional sterilization and lyophilization methodologies known to those skilled in the art.

Lyophilization aids useful in the embolization kits include but are not limited to mannitol, lactose, sorbitol, dextran, Ficoll, and polyvinylpyrrolidine(PVP). Stabilization aids useful in the embolization kits include but are not limited to ascorbic acid, cysteine, monothioglycerol, sodium bisulfite, sodium metabisulfite, gentisic acid, and inositol. Bacteriostats useful in the embolization kits include but are not limited to benzyl alcohol, benzalkonium chloride, chlorobutanol, and methyl, propyl or butyl paraben. A component in an embolization kit can also serve more than one function. A reducing agent can also serve as a stabilization aid, a buffer can also serve as a transfer ligand, a lyophilization aid can also serve as a transfer, ancillary or co-ligand and so forth.

The predetermined amounts of each component of an embolization kit are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the end-user of the embolization kit may practice the embolization methods of the invention with a high degree of certainty that the subject will not be harmed.

The embolization kits also contain written instructions for the practicing end-user. These instructions may be affixed to one or more of the vials or to the container in which the vial or vials are packaged for shipping or may be a separate insert, termed the package insert.

Definitions

For convenience, certain terms employed in the specification, examples, and appended claims are collected here.

The articles "a" and "an" are used herein to refer to one or to more than one (i.e. to at least one) of the grammatical object of the article. By way of example, "an element" means one element or more than one element.

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

The term "crosslinking agent", as used herein, refers to any chemical agent that joins adjacent chains of a polymer through covalent bonds.

The term "linkage" is used to refer to groups that normally are formed as the result of a chemical reaction and typically are covalent linkages. Hydrolytically stable linkages means that the linkages are stable in water and do not react with water at useful pHs for an extended period of time, potentially indefinitely. Hydrolytically unstable linkages are those that react with water, typically causing degradation of a hydrogel. Such a linkage is said to be subject to hydrolysis and to be hydrolyzable.

As used herein, the term "polymer" means a molecule, formed by the chemical union of two or more oligomer units.

The chemical units are normally linked together by covalent linkages. The two or more combining units in a polymer can be all the same, in which case the polymer is referred to as a homopolymer. They can be also be different and, thus, the polymer will be a combination of the different units. These polymers are referred to as copolymers.

The term "oligomer" is used herein to mean a molecule, typically an organic molecule, which in itself is formed by the chemical union of two or more monomer units. The monomer units of an oligomer may be different or all the same. An oligomer is capable of reacting with another oligomer which is same or different, in a polymerization reaction to form a polymer. As used herein, the term oligomer by no means limits the size of the molecule or the number of combining units or monomers in the oligomer. Rather, "oligomer" is used to indicate a unit for forming a polymer of the invention. The structure of an oligomer in a polymer may be somewhat different in chemical structure from the oligomer prior to polymerization because of the polymerization reaction and the formation of covalent linkages.

The term "biocompatible", as used herein, refers to having the property of being biologically compatible by not producing a toxic, injurious, or immunological response in living tissue.

The term "degradable", as used herein, refers to having the property of breaking down or degrading under certain conditions, e.g., at neutral or basic pH.

The term "gel", as used herein, refers to a colloid in which the disperse phase has combined with the dispersion medium to produce a semisolid material.

The term "colloid", as used herein, refers to a suspension of finely divided particles in a continuous medium in which the particles are approximately 5 to 5,000 angstroms in size.

The term "hydrogel", as used herein refers to a type of gel in which the disperse phase has combined with water to produce a semisolid material.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$ ed.*; Wiley: New York, 1991).

For purposes of this invention, the chemical elements are identified in accordance with the Periodic Table of the Elements, CAS version, Handbook of Chemistry and Physics, 67th Ed., 1986-87, inside cover.

Methods of the Invention

In certain embodiments, the present invention relates to a method of embolizing a vascular site in a mammal, comprising the step of:

introducing into the vasculature of a mammal a microparticle comprising a hydrolytically degradable crosslinked hydrogel, thereby embolizing a vascular site of said mammal.

In certain embodiments, the present invention relates to the aforementioned method of embolizing a vascular site in a mammal, wherein said hydrolytically degradable crosslinked hydrogel comprises a crosslink that substantially hydrolyzes only at about physiological pH.

In certain embodiments, the present invention relates to the aforementioned method of embolizing a vascular site in a mammal, wherein said hydrolytically degradable crosslinked hydrogel comprises a crosslink that does not substantially hydrolyze at a pH below about 5.

In certain embodiments, the present invention relates to the aforementioned method of embolizing a vascular site in a mammal, wherein said hydrolytically degradable crosslinked hydrogel comprises a crosslink comprising an O-acyl hydroxamic acid.

In certain embodiments, the present invention relates to the aforementioned method of embolizing a vascular site in a mammal, wherein said hydrolytically degradable crosslinked hydrogel comprises an acrylic acid, acrylate, or acrylamide.

In certain embodiments, the present invention relates to the aforementioned method of embolizing a vascular site in a mammal, wherein said hydrolytically degradable crosslinked hydrogel comprises acrylic acid, 2-hydroxyethyl acrylate, oligo(ethylene glycol) 2-methacrylate, acrylamide, N,N-dimethylacrylamide, or N-(tris(hydroxymethyl)methyl)acrylamide.

In certain embodiments, the present invention relates to the aforementioned method of embolizing a vascular site in a mammal, wherein said hydrolytically degradable crosslinked hydrogel comprises a first acrylamide and a second acrylamide.

In certain embodiments, the present invention relates to the aforementioned method of embolizing a vascular site in a mammal, wherein said hydrolytically degradable crosslinked hydrogel comprises a first acrylamide and a second acrylamide, wherein said first acrylamide is acrylamide or N,N-dimethylacrylamide.

In certain embodiments, the present invention relates to the aforementioned method of embolizing a vascular site in a mammal, wherein said hydrolytically degradable crosslinked hydrogel comprises a first acrylamide and a second acrylamide, wherein said second acrylamide is N-(tris(hydroxymethyl)methyl)acrylamide.

In certain embodiments, the present invention relates to the aforementioned method of embolizing a vascular site in a mammal, wherein said hydrolytically degradable crosslinked hydrogel comprises a first acrylamide and a second acrylamide, wherein said first acrylamide is acrylamide or N,N-dimethylacrylamide; and said second acrylamide is N-(tris(hydroxymethyl)methyl)acrylamide.

In certain embodiments, the present invention relates to the aforementioned method of embolizing a vascular site in a mammal, wherein said hydrolytically degradable crosslinked hydrogel comprises an acrylamide and an acrylate.

In certain embodiments, the present invention relates to the aforementioned method of embolizing a vascular site in a mammal, wherein said hydrolytically degradable crosslinked hydrogel comprises an acrylamide and an acrylate, wherein said acrylamide is acrylamide or N,N-dimethylacrylamide.

In certain embodiments, the present invention relates to the aforementioned method of embolizing a vascular site in a mammal, wherein said hydrolytically degradable crosslinked hydrogel comprises an acrylamide and an acrylate, wherein said acrylate is acrylic acid, 2-hydroxyethyl acrylate, or oligo(ethylene glycol) 2-methacrylate.

In certain embodiments, the present invention relates to the aforementioned method of embolizing a vascular site in a mammal, wherein said hydrolytically degradable crosslinked hydrogel comprises an acrylamide and an acrylate, wherein said acrylamide is acrylamide or N,N-dimethylacrylamide; and said acrylate is acrylic acid, 2-hydroxyethyl acrylate, or oligo(ethylene glycol) 2-methacrylate.

In certain embodiments, the present invention relates to the aforementioned method of embolizing a vascular site in a mammal, wherein said hydrolytically degradable crosslinked hydrogel comprises a first acrylate and a second acrylate.

In certain embodiments, the present invention relates to the aforementioned method of embolizing a vascular site in a mammal, wherein said hydrolytically degradable crosslinked hydrogel comprises a first acrylate and a second acrylate, wherein said first acrylate is acrylic acid, 2-hydroxyethyl acrylate, or oligo(ethylene glycol) 2-methacrylate.

In certain embodiments, the present invention relates to the aforementioned method of embolizing a vascular site in a mammal, wherein said hydrolytically degradable crosslinked hydrogel comprises a first acrylate and a second acrylate, wherein said first acrylate is acrylic acid, 2-hydroxyethyl acrylate, or oligo(ethylene glycol) 2-methacrylate; and said second acrylate is acrylic acid, 2-hydroxyethyl acrylate, or oligo(ethylene glycol) 2-methacrylate.

In certain embodiments, the present invention relates to the aforementioned method of embolizing a vascular site in a mammal, wherein said hydrolytically degradable crosslinked hydrogel comprises a crosslink derived from a compound represented by 1:

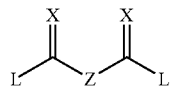

wherein

X represents independently for each occurrence O or S;

L represents independently for each occurrence —NH—O-Q, or —O—NH-Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_n$C(O)—, 2-alkylacryloylO$(CR_2)_n$C(O)—, 3-alkylacryloylO$(CR_2)_n$C(O)—, 2,3-dialkylacryloylO$(CR_2)_n$C(O)—, 3,3-dialkylacryloylO$(CR_2)_n$C(O)—, 2,3,3-trialkylacryloylO$(CR_2)_n$C(O)—, (diene)C(O)—, (vinyl)$(CR_2)_n$C(O)—, or (vinyl)ArC(O)—;

R represents independently for each occurrence H or alkyl;

Z represents $(CR_2)_n$, $(CR_2)_n J(CR_2)_m$, or $(CR_2)_n Ar(CR_2)_m$;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

n represents independently for each occurrence an integer in the range 1-10; and m represents independently for each occurrence an integer in the range 0-10.

In certain embodiments, the present invention relates to the aforementioned method of embolizing a vascular site in a mammal, wherein said hydrolytically degradable crosslinked hydrogel comprises a crosslink derived from a compound represented by 1, wherein X represents O.

In certain embodiments, the present invention relates to the aforementioned method of embolizing a vascular site in a mammal, wherein said hydrolytically degradable crosslinked hydrogel comprises a crosslink derived from a compound represented by 1, wherein L represents —NH—O-Q.

In certain embodiments, the present invention relates to the aforementioned method of embolizing a vascular site in a mammal, wherein said hydrolytically degradable crosslinked hydrogel comprises a crosslink derived from a compound represented by 1, wherein Q represents acryloyl, or 2-methacryloyl.

In certain embodiments, the present invention relates to the aforementioned method of embolizing a vascular site in a mammal, wherein said hydrolytically degradable crosslinked hydrogel comprises a crosslink derived from a compound represented by 1, wherein R represents H.

In certain embodiments, the present invention relates to the aforementioned method of embolizing a vascular site in a mammal, wherein said hydrolytically degradable crosslinked hydrogel comprises a crosslink derived from a compound represented by 1, wherein Z represents $(CR_2)_n$.

In certain embodiments, the present invention relates to the aforementioned method of embolizing a vascular site in a mammal, wherein said hydrolytically degradable crosslinked hydrogel comprises a crosslink derived from a compound represented by 1, wherein X represents O; and L represents —NH—O-Q.

In certain embodiments, the present invention relates to the aforementioned method of embolizing a vascular site in a mammal, wherein said hydrolytically degradable crosslinked hydrogel comprises a crosslink derived from a compound represented by 1, wherein X represents O; L represents —NH—O-Q; and Q represents acryloyl, or 2-methacryloyl.

In certain embodiments, the present invention relates to the aforementioned method of embolizing a vascular site in a mammal, wherein said hydrolytically degradable crosslinked hydrogel comprises a crosslink derived from a compound represented by 1, wherein X represents O; L represents —NH—O-Q; Q represents acryloyl, or 2-methacryloyl; and R represents H.

In certain embodiments, the present invention relates to the aforementioned method of embolizing a vascular site in a mammal, wherein said hydrolytically degradable crosslinked hydrogel comprises a crosslink derived from a compound represented by 1, wherein X represents O; L represents —NH—O-Q; Q represents acryloyl, or 2-methacryloyl; R represents H; and Z represents $(CR_2)_n$.

In certain embodiments, the present invention relates to the aforementioned method of embolizing a vascular site in a mammal, wherein said hydrolytically degradable crosslinked hydrogel comprises a crosslink derived from a compound represented by 2:

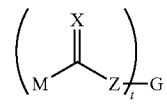

wherein

X represents independently for each occurrence O or S;

M represents independently for each occurrence —NH—O-Q, or —O—NH-Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_n$C(O)—, 2-alkylacryloylO$(CR_2)_n$C(O)—, 3-alkylacryloylO$(CR_2)_n$C(O)—, 2,3-dialkylacryloylO$(CR_2)_n$C(O)—, 3,3-dialkylacryloylO$(CR_2)_n$C(O)—, 2,3,3-trialkylacryloylO$(CR_2)_n$C(O)—, (diene)C(O)—, (vinyl)$(CR_2)_n$C(O)—, or (vinyl)ArC(O)—;

R represents independently for each occurrence H or alkyl;

Z represents $(CR_2)_n$, $(CR_2)_n J(CR_2)_m$, or $(CR_2)_n Ar(CR_2)_m$;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

G represents $(CR_{(4-t)})$, aryl, or heteroaryl;

n represents independently for each occurrence an integer in the range 1-10; and t represents 3 or 4.

In certain embodiments, the present invention relates to the aforementioned method of embolizing a vascular site in a mammal, wherein said hydrolytically degradable crosslinked hydrogel comprises a crosslink derived from a compound represented by 2, wherein X represents O.

In certain embodiments, the present invention relates to the aforementioned method of embolizing a vascular site in a mammal, wherein said hydrolytically degradable crosslinked hydrogel comprises a crosslink derived from a compound represented by 2, wherein M represents —NH—O-Q.

In certain embodiments, the present invention relates to the aforementioned method of embolizing a vascular site in a mammal, wherein said hydrolytically degradable crosslinked hydrogel comprises a crosslink derived from a compound represented by 2, wherein Q represents acryloyl, or 2-methacryloyl.

In certain embodiments, the present invention relates to the aforementioned method of embolizing a vascular site in a mammal, wherein said hydrolytically degradable crosslinked hydrogel comprises a crosslink derived from a compound represented by 2, wherein R represents H.

In certain embodiments, the present invention relates to the aforementioned method of embolizing a vascular site in a mammal, wherein said hydrolytically degradable crosslinked hydrogel comprises a crosslink derived from a compound represented by 2, wherein X represents O; and M represents —NH—O-Q.

In certain embodiments, the present invention relates to the aforementioned method of embolizing a vascular site in a mammal, wherein said hydrolytically degradable crosslinked hydrogel comprises a crosslink derived from a compound represented by 2, wherein X represents O; M represents —NH—O-Q; and Q represents acryloyl, or 2-methacryloyl.

In certain embodiments, the present invention relates to the aforementioned method of embolizing a vascular site in a mammal, wherein said hydrolytically degradable crosslinked hydrogel comprises a crosslink derived from a compound represented by 2, wherein X represents O; M represents —NH—O-Q; Q represents acryloyl, or 2-methacryloyl; and R represents H.

In certain embodiments, the present invention relates to the aforementioned method of embolizing a vascular site in a mammal, wherein said hydrolytically degradable crosslinked hydrogel comprises a crosslink derived from a compound represented by 3:

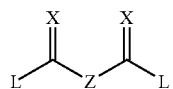

3 wherein
X represents independently for each occurrence O or S;
L represents independently for each occurrence —O—NH-Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_n$C(O)—, 2-alkylacryloylO$(CR_2)_n$C(O)—, 3-alkylacryloylO$(CR_2)_n$C(O)—, 2,3-dialkylacryloylO$(CR_2)$C(O)—, 3,3-dialkylacryloylO$(CR_2)_n$C(O)—, 2,3,3-trialkylacryloylO$(CR_2)_n$C(O)—, (diene)C(O)—, (vinyl)$(CR_2)_n$C(O)—, or (vinyl)ArC(O)—;
R represents independently for each occurrence H or alkyl;
Z represents —NH$(CR_2)_n$NH—, or —NH$(CR_2)_n$J$(CR_2)_n$NH—;
Ar represents independently for each occurrence aryl or heteroaryl;
J represents independently for each occurrence O, S, NR, cycloalkyl, heterocyclyl, $(CH_2CH_2O)_n$, or $(CH_2CH_2N(R))_n$;
n represents independently for each occurrence an integer in the range 1-10; and
m represents independently for each occurrence an integer in the range 0-10.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein X represents O.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein L represents —O—NH-Q.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein Q represents acryloyl, or 2-methacryloyl.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein R represents H.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein Z represents —NH$(CR_2)_n$NH—.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein X represents O; and L represents —O—NH-Q.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein X represents O; L represents —O—NH-Q; and Q represents acryloyl, or 2-methacryloyl.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein X represents O; L represents —O—NH-Q; Q represents acryloyl, or 2-methacryloyl; and R represents H.

In certain embodiments, the present invention relates to the aforementioned method of embolizing a vascular site in a mammal, wherein said hydrolytically degradable crosslinked hydrogel comprises a crosslink derived from a compound represented by 3 and the attendant definitions, wherein X represents O; L represents —O—NH-Q; Q represents acryloyl, or 2-methacryloyl; R represents H; and Z represents —NH$(CR_2)_n$NH—.

In certain embodiments, the present invention relates to the aforementioned method of embolizing a vascular site in a mammal, wherein said hydrolytically degradable crosslinked hydrogel comprises a crosslink derived from a compound represented by 4:

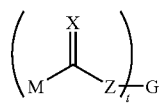

wherein
X represents independently for each occurrence O or S;
M represents independently for each occurrence —O—NH-Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_n$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
G represents (CR$_{(4-t)}$), aryl, or heteroaryl;
n represents independently for each occurrence an integer in the range 1-10;
m represents independently for each occurrence an integer in the range 0-10; and
t represents 3 or 4.

In certain embodiments, the present invention relates to the aforementioned method of embolizing a vascular site in a mammal, wherein said hydrolytically degradable crosslinked hydrogel comprises a crosslink derived from a compound represented by 4 and the attendant definitions, wherein X represents O.

In certain embodiments, the present invention relates to the aforementioned method of embolizing a vascular site in a mammal, wherein said hydrolytically degradable crosslinked hydrogel comprises a crosslink derived from a compound represented by 4 and the attendant definitions, wherein M represents —O—NH-Q.

In certain embodiments, the present invention relates to the aforementioned method of embolizing a vascular site in a mammal, wherein said hydrolytically degradable crosslinked hydrogel comprises a crosslink derived from a compound represented by 4 and the attendant definitions, wherein Q represents acryloyl, or 2-methacryloyl.

In certain embodiments, the present invention relates to the aforementioned method of embolizing a vascular site in a mammal, wherein said hydrolytically degradable crosslinked hydrogel comprises a crosslink derived from a compound represented by 4 and the attendant definitions, wherein R represents H.

In certain embodiments, the present invention relates to the aforementioned method of embolizing a vascular site in a mammal, wherein said hydrolytically degradable crosslinked hydrogel comprises a crosslink derived from a compound represented by 4 and the attendant definitions, wherein X represents O; and M represents —O—NH-Q.

In certain embodiments, the present invention relates to the aforementioned method of embolizing a vascular site in a mammal, wherein said hydrolytically degradable crosslinked hydrogel comprises a crosslink derived from a compound represented by 4 and the attendant definitions, wherein X represents O; M represents —O—NH-Q; and Q represents acryloyl, or 2-methacryloyl.

In certain embodiments, the present invention relates to the aforementioned method of embolizing a vascular site in a mammal, wherein said hydrolytically degradable crosslinked hydrogel comprises a crosslink derived from a compound represented by 4 and the attendant definitions, wherein X represents O; M represents —O—NH-Q; Q represents acryloyl, or 2-methacryloyl; and R represents H.

In certain embodiments, the present invention relates to the aforementioned method of embolizing a vascular site in a mammal, wherein said vascular site is proximal to a hemorrhage, cancerous tissue, a uterine fibroid, a tumor, or an organ.

In certain embodiments, the present invention relates to the aforementioned method of embolizing a vascular site in a mammal, wherein said hydrolytically degradable crosslinked hydrogel embolizes said vascular site for less than about three months.

In certain embodiments, the present invention relates to the aforementioned method of embolizing a vascular site in a mammal, wherein said hydrolytically degradable crosslinked hydrogel embolizes said vascular site for less than about two months.

In certain embodiments, the present invention relates to the aforementioned method of embolizing a vascular site in a mammal, wherein said hydrolytically degradable crosslinked hydrogel embolizes said vascular site for less than about one month.

In certain embodiments, the present invention relates to the aforementioned method of embolizing a vascular site in a mammal, wherein said hydrolytically degradable crosslinked hydrogel embolizes said vascular site for less than about fourteen days.

In certain embodiments, the present invention relates to the aforementioned method of embolizing a vascular site in a mammal, wherein said hydrolytically degradable crosslinked hydrogel embolizes said vascular site for less than about seven days.

In certain embodiments, the present invention relates to the aforementioned method of embolizing a vascular site in a mammal, wherein said hydrolytically degradable crosslinked hydrogel embolizes said vascular site for less than about three days.

In certain embodiments, the present invention relates to the aforementioned method of embolizing a vascular site in a mammal, wherein said hydrolytically degradable crosslinked hydrogel embolizes said vascular site for less than about one day.

In certain embodiments, the present invention relates to the aforementioned method of embolizing a vascular site in a mammal, wherein said microparticle further comprises a contrast-enhancing agent.

In certain embodiments, the present invention relates to the aforementioned method of embolizing a vascular site in a mammal, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned method of embolizing a vascular site in a mammal, wherein said microparticle further comprises a biologically active agent.

In certain embodiments, the present invention relates to the aforementioned method of embolizing a vascular site in a mammal, wherein said mammal is a primate, equine, canine or feline.

In certain embodiments, the present invention relates to the aforementioned method of embolizing a vascular site in a mammal, wherein said mammal is a human.

In certain embodiments, the present invention relates to the aforementioned method of embolizing a vascular site in a mammal, wherein said microparticle is introduced into the vasculature of said mammal using a catheter.

In certain embodiments, the present invention relates to the aforementioned method of embolizing a vascular site in a mammal, wherein said microparticle is a sphere, rod, plug, or coil.

In certain embodiments, the present invention relates to the aforementioned method of embolizing a vascular site in a mammal, wherein said microparticle is a sphere.

In certain embodiments, the present invention relates to the aforementioned method of embolizing a vascular site in a mammal, wherein said microparticle is a sphere having a diameter in the range of 10-5,000 µm inclusive.

In certain embodiments, the present invention relates to the aforementioned method of embolizing a vascular site in a mammal, wherein said microparticle is a sphere having a diameter in the range of 40-3,000 µm inclusive.

EXEMPLIFICATION

The invention now being generally described, it will be more readily understood by reference to the following examples, which are included merely for purposes of illustration of certain aspects and embodiments of the present invention, and are not intended to limit the invention.

Example 1

Preparation of Glutaroyl Dihydroxamic Acid (C5NHOH)

The dihydroxamic acids were prepared through the reaction between the corresponding diester and hydroxylamine. For instance, the reaction of dimethyl glutarate (DBE-5, dibasic ester) with hydroxylamine produced C5NHOH. In a 1000 mL breaker containing 400 mL of methanol, DBE-5 (100 g, 0.6 mol) was added with stirring. This was followed by the addition of an aqueous solution of hydroxylamine (88.8 g, 50 wt % in water; 1.34 mol). This reaction was allowed to proceed for 85 h at room temperature. Then, the resulting C5NHOH was precipitated by introducing 400 mL of ethanol into the above reaction mixture, filtrated under vacuum and washed three times with ethanol. The product thus obtained was vacuum-dried at 40° C. for more than 48 h and a white powder was obtained with a yield of 66% based on the feed amount of DBE-5. 1H NMR measurement indicated that the peak at 3.68 ppm due to the methyl ester groups of DBE-5 disappeared completely after reaction and two new peaks corresponding to —NH— (10.37 ppm) and —OH (8.68 ppm) emerged quantitatively. Therefore, the ester groups were changed to hydroxamic acid groups completely.

Example 2

Preparation of Malonyl Dihydroxamic Acid (C3NHOH)

Malonyl dihydroxylamic acid was prepared according to the procedure outlined in Example 1, but with dimethyl malonate instead of dimethyl glutarate.

Example 3

Preparation of Succinyl Dihydroxamic Acid (C4NHOH)

Succinyl dihydroxylamic acid was prepared according to the procedure outlined in Example 1, but with dimethyl succinate instead of dimethyl glutarate.

Example 4

Preparation of Adipoyl Dihydroxamic Acid (C6NHOH)

C6NHOH was prepared by reacting dimethyl adipate (DBE-6, dibasic ester) with hydroxylamine in a mixture of methanol and water at room temperature. In a 1000 mL flask containing a magnetic stirring bar, methanol (500 mL) and DBE-6 (143 g, 0.813 mol) were sequentially added. The reaction started by introducing an aqueous solution of hydroxylamine (124 g of 50 wt % aqueous solution, 1.87 mol) into the above system. After the reaction proceeded for 48 h at room temperature, the mixture was concentrated by using a rotavapor and the product precipitated gradually. C6NHOH thus prepared was washed with cooled water (4° C.) three times. After vacuum-drying at 45° C. for 72 h, a white solid was obtained with a yield of 88% based on the feed amount of DBE-6 and its $^1$H NMR spectrum was consistent with the molecular structure of C6NHOH.

Example 5

Synthesis of N,N'-(dimethacryloyloxy)glutarylamide (C5NCL)

C5NCL was synthesized via the reaction between C5NHOH (prepared according to Example 1) and methacryloyl chloride. Well-dried glassware was used immediately after being taken out from the oven (120° C.). A four-neck 1000 mL round-bottom flask was equipped with a paddle stir, a dropping funnel with a pressure-equalization arm, a condenser and a thermometer. This reactor was degassed and replaced with nitrogen twice. Under nitrogen, well-dried C5NHOH (32.4 g, 0.20 mol) was first added, and this was followed by the addition of well-dried pyridine (50 mL) and DMF (260 mL). Then, methacryloyl chloride (41.4 mL, 0.4 mol) was diluted with DMF (40 mL) and added dropwise very slowly through the dropping funnel. After the reaction lasted 3 h at room temperature, 300 mL of chloroform was added and this mixture was poured into a large quantity of water (ca. 1000 mL) with vigorous starring. The organic phase was washed with water three times, dried with MgSO4 overnight and concentrated by evaporating chloroform off. Then, C5NHOH was obtained via crystallization from a mixture of ethyl ether and hexane. After vacuum-drying at 35° C. for 24 h, a white soft crystal was obtained with a yield of 34%. 1H NMR measurement indicated that after reaction, the resonance due to the hydroxyl group (8.68 ppm) of C5NHOH disappeared completely. The new peaks corresponding to the methacryloyl groups ($CH_2=$, 5.86 and 6.16 ppm; —$CH_3$, 1.94 ppm) emerged quantitatively, and the peak corresponding to —NH— group shifted from 10.37 to 11.71 ppm. The above results confirmed the formation of the new crosslinker C5NCL with designed molecular structure.

Example 6

Synthesis of N,N'-(dimethacryloyloxy)malonylamide (C3NCL)

Crosslinker N,N'-(dimethacryloyloxy)malonamide (C3NCL) was prepared according to the procedure outlined in Example 5, but with malonyl dihydroxamic acid (C3NHOH) prepared according to Example 2.

Example 7

Synthesis of N,N'-(dimethacryloyloxy)succinylamide (C4NCL)

Crosslinker N,N'-(dimethacryloyloxy)succinamide (C4NCL) was prepared according to the procedure outlined in Example 5, but with succinyl dihydroxamic acid (C4NHOH) prepared according to Example 3.

Example 8

Synthesis of N,N'-(dimethacryloyloxy)adipamide (C6NCL)

Using an apparatus similar to that for the preparation of C5NCL, C6NCL was prepared by reacting C6NHOH with methacryloyl chloride. C6NHOH (17.6 g, 0.1 mol) and a mixture of DMF (150 mL) and pyridine (40 mL) were charged first. Methacryloyl chloride (22 mL, 0.21 mol) was dissolved in 20 mL DMF and this solution was dropwise added within 35 min with stirring. After this reaction was allowed to last 2 h at 35° C., 200 mL of chloroform was added to dilute the reaction mixture. Then, 15 mL of concentrated hydrochloric acid was diluted with 200 mL of water and this solution was transferred into the above reaction system. In this manner, the mixture was separated to water and organic phases. The water phase was extracted with 50 mL of chloroform and this was combined with the organic phase. This chloroform solution was washed with water three times and dried with $MgSO_4$ overnight. When concentrated by evaporating, C6NCL precipitated as a white crystal, which was washed with ethyl ether twice and vacuum-dried overnight at 35° C. (yield: 38%). Its molecular structure and high purity (>99%) were confirmed by $^1H$ NMR.

Example 9

Preparation of Hydrogels in Water

The crosslinkers of the present invention may be used for the synthesis of hydrogels in water or in an organic solvent or in mixture of aqueous and organic solvents. Here is an example for the preparation of 2-hydroxyethyl acrylate (HEA) hydrogel in water. C5NCL was first dissolved in DMF to obtain a 25 wt % solution. In a 100 mL round-bottom flask, HEA (2.0 g), C5NCL (0.4 g of 25 wt % DMF solution) and a mixed solvent (20 g) of glycerol and water (1:1 by volume) were added. This system was degassed, then re-filled with nitrogen twice. This flask was placed in an oil bath kept at 55° C. The polymerization was started by sequentially adding the initiator ammonium persulfate (APS, 50 mg) and the accelerator N,N,N,N-tetramethylethylenediamine (TMEDA, 0.1 mL). The hydrogel formed immediately and it was immersed in ethanol overnight, washed with ethanol and vacuum-dried for 20 h. As shown in Table 1, a series of hydrogels were prepared from different monomers, such as N,N-dimethylacrylamide (DMA), acrylic acid (AA), acrylamide (AAm), N-[tris(hydroxymethyl)methyl]acrylamide (TS), N-(hydroxymethyl)methacrylamide (HMMA), sodium acrylate (NaAA), and poly(ethylene glycol)-methacrylate (MW average 526).

TABLE 1

Hydrogels prepared in water[a]

| Monomer | Crosslinker | Physiological Degradation Time[b] | Storage Degradation Time[c] |
|---|---|---|---|
| TS | C5NCL | 22 days | None detected |
| HEA | C5NCL | 26 days | None detected |
| HMMA | C6NCL | 20 days | None detected |
| PEG-macromer | C6NCL | 31 days | None detected |
| AA | C5NCL | 8 h | None detected |
| NaAA | C6NCL | 6 h | None detected |
| DMA | C6NCL | 32 h | None detected |
| AAm | C6NCL | 7 h | None detected |

[a] Hydrogel formed with 5% crosslinker at 55° C.
[b] pH = 7.4, 37° C.
[c] pH = 2; 5° C.; >2 months.

Example 10

Preparation of Copolymer Hydrogels

Under the conditions similar to those for homopolymer hydrogels, the copolymerization of two monomers in the presence of the new crosslinker generated corresponding copolymer hydrogels. Here is an example for the preparation of TS-AA copolymer hydrogel. In a 100 mL round-bottom flask containing a magnetic stirring bar, 1.8 g of TS was charged. This solid monomer was dissolved in a mixed solvent (20 g) of glycerol and distilled water (2:1 by volume). Then, AA (0.2 g) and C5NCL (0.4 g of 25 wt % DMF solution) were added at room temperature. This system was degassed under reduced pressure and replaced with nitrogen twice. When the temperature was raised to 60° C., APS (50 mg) and TMEDA (0.1 mL) were sequentially added to induce the polymerization. The copolymer hydrogel formed instantaneously, which was immersed in ethanol to remove the solvent, washed with ethanol and vacuum-dried over 20 h. Using a similar procedure, TS-AA and TS-DMA copolymer hydrogels with various compositions were prepared (see Table 2).

TABLE 2

Copolymer hydrogels[a].

| Monomer 1 | Monomer 2 | Physiological Degradation Time[b] | Storage Degradation Time[c] |
|---|---|---|---|
| HEA 90% | DMA 10% | 13 days | None detected |
| HEA 80% | DMA 20% | 9.5 days | None detected |
| HEA 90% | AA 10% | 4 days | None detected |
| PEA 80% | AA 20% | 2 days | None detected |
| TS 90% | DMA 10% | 7 days | None detected |
| TS 80% | DMA 20% | 4 days | None detected |
| TS 90% | AA 10% | 23 h | None detected |
| TS 80% | AA 20% | 15 h | None detected |

[a] Hydrogel formed with 5% C5NCL at 55° C.
[b] pH = 7.4 at 37° C.
[c] pH = 2; 5° C.; >2 months.

Example 11

Preparation of (hydro)gels in Organic Solvents

Because the crosslinkers are soluble in organic solvents, the hydrogels were also prepared in organic solvents. Here is an example of 2-hydroxyethl methacrylate (HEMA) hydrogel prepared in 1,4-dioxane. In a 100 mL round-bottom flask containing a magnetic stirring bar, HEMA (2.2 g) was dissolved in 1,4-dioxane (10 g). To this flask, C6NCL (2.2 g of 10 wt % DMF solution) was added. This system was degassed under reduced pressure and replaced with nitrogen twice. When the temperature was raised to 60° C., 2,2'-anobisisobutyronitrile (AIBN, 35 mg in 1 mL of 1,4-dioxane) was added to induce the polymerization. The copolymer hydrogel formed in 65 min and the reaction was allowed to last additional 3 h. The hydrogel thus obtained was immersed in acetone to remove the solvent, washed with acetone and vacuum-dried overnight. Using a similar procedure, several kinds of hydrogels were prepared from different monomers, such as t-butyl acrylamide (BAA) and mono-2-(acryloyloxy) ethyl succinate (AES) (see Table 3).

TABLE 3

Hydrogels prepared in organic solvent[a]

| Monomer | Crosslinker |
|---------|-------------|
| HEMA 2.2 g | C6NCL 0.22 g |
| AES 2.0 g | C6NCL 0.18 g |
| BAA 2.3 g | C5NCL 0.15 g |

[a]Hydrogels prepared in 1,4-dioxane at 60° C.

Example 12

Preparation of TS Homopolymer Beads

A 500 mL open-mouth jacketed flask was equipped with a mixer, a thermometer and a temperature controller, to which 150 mL of mineral oil and 0.12 g of sorbitan sesquioleate (SSO) were sequentially added. This system was heated to 60° C. by circulating water with stirring (350 rpm), and used as the continuing oil phase.

Simultaneously, the water phase was prepared in a small beaker as follows. Sodium chloride (23.2 g) and sodium acetate (11.0 g) were first dissolved in distilled water (81.6 mL). Then, this aqueous solution was mixed with glycerol (163 mL) with magnetic stirring. Finally, the pH value of this mixture was regulated to 6.0 by adding acetic acid.

The buffer solution (pH =6, 26 mL) was used to dissolve TS (5.0 g). To this solution, the crosslinker C6NCL (0.3 g in 3.0 g DMF solution) was dropwise added with stirring. This mixture was heated to 60° C. in an oil bath. As soon as the initiator APS (0.2 g) was added, this water phase was transferred into the oil phase with fast stirring (650 rpm), and TMEDA (0.4 mL) was added immediately to accelerate the reaction. After the polymerization lasted 1 h, the mixture was rinsed into about 120 mL of water to separate the beads. The beads in water phase were washed with water for more than five times, then, immersed in a buffer (pH =2) and stored in the refrigerator (4° C.). [Bead size and distribution, minimum: 16.8; maximum: 793.1; D1,0 (Num. mean): 181.3; D2,0: 207.3; D4,3 (Vol. mean): 330.5]. In the buffer solution (pH =7.4) at 37° C., this type of bead degraded completely in 21 days.

Example 13

Preparation of TS-DMA Copolymer Beads

The oil phase preparation was carried out according to the procedure outlined in Example 12. However, instead of using one monomer, both TS and DMA were included in the water phase. TS constitutes the neutral polymer backbone, while DMA acts as the degradation controller. For instance, 4.5 g of TS was first dissolved in the buffer solution (26 g, pH =6. see Example 12) at 45° C. Then, 0.50 g of DMA and a DMF solution of the crosslinker C6NCL (10 wt %, 3 g) were dropwise added with stirring. This system was heated to 60° C. in an oil bath. Upon the addition of 0.20 g of APS, this mixture was poured into the oil phase and the accelerator TMEDA (0.40 mL dissolved in 2 mL mineral oil) was added immediately. About 1 h later, the beads thus obtained were purified in the way similar to that used in Example 8. [Bead size and distribution, minimum: 16.8; maximum: 893.3; D1,0 (Num. mean): 229.4; D2,0: 281.4; D4,3 (Vol. mean): 476.7]. In the buffer solution (pH =7.4) at 37° C., this type of bead degraded completely in 7 days.

Example 14

Preparation of Citroyl Trihydroxamic Acid (CTA)

Citroyl trihydroxamic acid (CTA) was synthesized through the exchange reaction between triethyl citrate and hydroxylamine. In a 1000 mL beaker with a paddle stirrer, methanol (400 mL) and triethyl citrate (112 g, 0.40 mol) were sequentially added. Then, the reaction was started by introducing an aqueous solution of hydroxylamine (50 wt %, 87 g, 1.3 mol) into the above mixture with stirring at room temperature. As the reaction was proceeding, the product, CTA, precipitated gradually. After 72 h, the solid CTA thus obtained was washed twice with methanol and vacuum-dried for 50 h at 45° C. Yield: 54% (based on the feed amount of triethyl citrate). $^1$H NMR spectra showed no peaks corresponding to an ethyl ester group; further, a very broad peak (5.35-11.00 ppm) was observed, corresponding to the N—H and O—H moieties of the hydroxamic acid groups.

Example 15

Preparation of Three-arm Star-Shaped Crosslinker, N,N,N-(trimethacryloyloxy)citrylamide (TMCA)

Using an apparatus similar to that for the preparation of C5NCL, the three-arm star-shaped crosslinker TMCA was synthesized. CTA was reacted with methacryloyl chloride (MCl). The molar ratio of MCl and CTA was roughly MCl/CTA=3.0. The general procedure was the same as that used in the synthesis of C5NCL. This star-shaped crosslinker was used for the preparation of both hydrogels and beads.

Example 16

Preparation of TS-DMA Copolymer Hydrogel by Using TMCA as Crosslinker

In a 100 mL round-bottom flask containing a magnetic stirring bar, 4.0 g of TS was added. This solid monomer was dissolved in a mixed solvent (40 g) of glycerol and distilled water (2:1 by volume). Then, DMA (1.0 g) and TMCA (1.0 g of 25 wt % DMF solution) were added at room temperature. This system was degassed under reduced pressure and replaced with nitrogen twice. The temperature was raised to 60° C., and APS (0.15 mg) and TMEDA (0.4 mL) were sequentially added to induce the polymerization. The copolymer hydrogel formed instantaneously, and was then immersed in ethanol to remove the solvent, washed with ethanol and vacuum-dried for 20 h. This hydrogel degraded in a buffer (pH =7.4) within 5 days at 37° C.

Example 17

Preparation of TS-DMA Copolymer Beads by Using TMCA as Crosslinker

The oil phase preparation was carried out according to the procedure described in Example 12. For the preparation of the water phase, 4.5 g of TS was first dissolved in a buffer solution (30 g, pH =6; see Example 12) at 45° C. Then, 0.50 g of DAM and a DMF solution of the crosslinker TMCA (25 wt %, 1.0 g) were added dropwise with stirring. This system was heated to 60° C. in an oil bath. Upon the addition of 0.15 g of APS, this mixture was poured into the oil phase and the accelerator TMEDA (0.40 mL dissolved in 2 mL mineral oil) was added. About 25 min later, the beads thus obtained were purified using the protocol described in Example 12. In a buffered solution (pH =7.4) at 37° C., the beads degraded completely in 4 days.

Example 18

Synthesis of N-methacryloylhydroxylamine (MHA)

MHA was synthesized by reacting methyl methacrylate (MMA) with hydroxylamine in a basic aqueous solution. In a 700 mL beaker, hydroxylamine hydrochloride (70 g) was added, which was dissolved in 150 g of sterile water. The aqueous solution thus obtained was cooled to 0° C., to which MMA (100 g) was added. In another beaker, sodium hydroxide (80 g) was dissolved in sterile water (140 g). After cooling to 0° C., this basic aqueous solution was dropwise added to the first beaker with vigorous stirring. At this stage, the formation of MHA was confirmed by testing the reaction mixture with an acidic aqueous solution of ferric chloride (The deep-red color of the complex formed between MHA and $FeCl_3$ appeared instantaneously). After the reaction lasted 3 h at 0° C., the system was concentrated by distillation under reduced pressure and the residue was extracted with ether (200 mL) for six times. The ether phase was concentrated by evaporation and a solid product was obtained by crystallization from a mixture of ether and hexane. The 1H NMR spectrum of this crystal is consistent with the molecular structure of MHA (in $DMSO-D_6$: —NHOH, 10.70 and 8.79 ppm; $C=CH_2$, 5.28 and 5.57 ppm; —$CH_3$, 1.82 ppm) and no impurity was detected.

Example 19

Synthesis of a Crosslinker: MHA-DIH

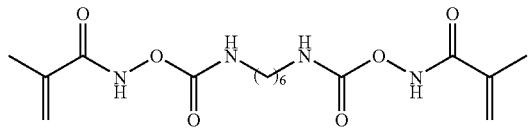

MHA-DIH is the adduct of one 1,6-diisocyanatohexane (DIH) molecule and two MHA molecules, which was prepared by reacting DIH with MHA in THF at room temperature. A well-dried 250 mL round-bottom flask containing a magnetic stirring bar was protected with nitrogen, to which MHA (11.1 g, 0.11 mol) was first added and this was followed by the addition of $CaH_2$-dried THF (40 g). After MHA dissolved completely, DIH (8.3 mL, 0.05 mol) was diluted with THF (16 g) and dropwise added with a dried syringe over 15 min. The reaction was allowed to last 24 h at room temperature with stirring. Then, the reaction system was concentrated by evaporating and put into the refrigerator for crystallization. The white crystal crosslinker MHA-DIH was obtained by filtration, washed with THF three times, and vacuum-dried overnight (Yield =46% based on the feed amount of DIH). Its very high purity was conformed by 1H NMR measurement (in $DMF-d_7$): 11.47 ppm, 2H, O=C—NHO; 7.58 ppm, 2H, O=C—NH—C; 5.47 and 5.80 ppm, 4H, $CH_2=$; 3.14 ppm, 4H, —$NHCH_2CH_2CH_2CH_2CH_2CH_2NH$—; 1.92 ppm, 6H, —$CH_3$; 1.50 ppm, 4H, —$NHCH_2CH_2CH_2CH_2CH_2CH_2NH$—; 1.33 ppm, 4H, $NHCH_2CH_2CH_2CH_2CH_2CH_2NH$—.

Example 20

Synthesis of a Crosslinker: MHA-DIB

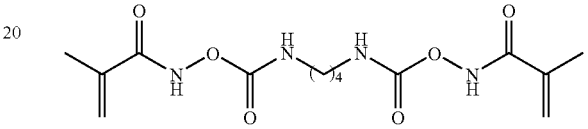

MHA-DIB is the adduct of one 1,4-diisocyanatobutane (DIB) molecule and two MHA molecules, which was prepared by reacting DIB with MHA in THF at room temperature. As described for the preparation of MHA-DIH, a similar synthetic procedure was also applied to MHA-DIB. A white crystal product was obtained with a yield of 39% based on the feed amount of DIB. Similar to that of MHA-DIH, its NMR spectrum is completely consistent with its molecular structure (in $DMF-d_7$): 11.48 ppm, 2H, O=C—NHO; 7.60 ppm, 2H, O=C—NH—C; 5.48 and 5.81 ppm, 4H, $CH_2=$; 3.16 ppm, 4H, $NHCH_2CH_2CH_2CH_2NH$; 1.93 ppm, 6H, —$CH_3$; 1.55 ppm, 4H, —$NHCH_2CH_2CH_2CH_2NH$—.

Example 21

Preparation of DMA Homopolymer Beads Using MHA-DIH as the Crosslinker

A 500 mL open-mouth jacketed flask was equipped with a mixer, a thermometer and a temperature controller, to which 150 mL of mineral oil and 0.12 g of sorbitan sesquioleate (SSO) were sequentially added. This system was heated to 60° C. by circulating water with stirring (350 rpm), and used as the continuing oil phase.

Simultaneously, the water phase was prepared in a small beaker as follows. Sodium chloride (23.2 g) and sodium acetate (11.0 g) were first dissolved in distilled water (81.6 mL). Then, this aqueous solution was mixed with glycerol (163 mL) with magnetic stirring. Finally, the pH value of this mixture was regulated to 6.0 by adding acetic acid.

The buffer solution (pH=6, 25 mL) was used to dissolve DMA (5.0 g). To this solution, the crosslinker MHA-DIH (25 w % DMF solution, 1.8 g) was dropwise added with stirring. This mixture was heated to 60° C. in an oil bath. As soon as the initiator APS (0.15 g) was added, this water phase was transferred into the oil phase with fast stirring (650 rpm), and TMEDA (0.4 mL) was added immediately to accelerate the reaction. After the polymerization lasted 30 min, the mixture was rinsed into about 120 mL of water (pH=3.0) to separate the beads. The beads in water phase were washed with water (pH=3) for more than five times, then, immersed in a buffer (pH=2) and stored in the refrigerator (4° C.). This kind of beads in the buffer solution (pH=7.4) degraded completely within 5 days at 37° C. As shown in Table 4, by using different monomers and/or crosslinker, several kinds of homopolymer beads were prepared.

TABLE 4

Preparation of homo- and co-polymer beads.

| Monomer 1 (%)[a] | Monomer 2 (%)[a] | Crosslinker (%)[b] | Degradation time at pH = 7.4[c] | Degradation time at pH = 2[d] |
|---|---|---|---|---|
| DMA 100 | | MHA-DIH 9 | 5 days | No degradation after 2 months |
| TS 100 | | MHA-DIH 9 | 1.5 days | No degradation after 2 months |
| HEA 100 | | MHA-DIH 9 | >16 days | No degradation after 2 months |
| DMA 80 | TS 20 | MHA-DIH 9 | 3 days | No degradation after 2 months |
| DMA 50 | TS 50 | MHA-DIH 9 | 1.5 days | No degradation after 2 months |
| DMA 80 | HEA 20 | MHA-DIH 9 | 3.5 days | No degradation after 2 months |
| DMA 50 | HEA 50 | MHA-DIH 9 | 7 days | No degradation after 2 months |
| DMA 100 | | MHA-DIB 9 | 2.5 days | No degradation after 2 months |
| TS 100 | | MHA-DIB 9 | 1 day | No degradation after 2 months |
| HEA 100 | | MHA-DIB 9 | >5 days | No degradation after 2 months |
| DMA 80 | TS 20 | MHA-DIB 9 | 1.5 days | No degradation after 2 months |
| DMA 50 | TS 50 | MHA-DIB 9 | 2.5 days | No degradation after 2 months |
| DMA 50 | HEA 50 | MHA-DIB 9 | 3 days | No degradation after 2 months |

[a]TS: [tris(hydroxymethyl)]methyl acrylate; HEA: 2-hydroxyethl methacrylate; DMA: N,N-dimethylacrylamide.
[b]Compared to the total amount of the monomer(s), 9 wt % of the crosslinker was used.
[c]At 37 C.
[d]At 5 C.

Example 22

Preparation of DMA-TS Copolymer Beads

The oil phase preparation was carried out in the same way as used in Example 5. However, instead of only one monomer, both TS and DMA were included in the water phase. 1.0 g of TS was first dissolved in the buffer solution (25 g, pH =6; see Example 5) at 45° C. Then, 4.0 g of DMA and a DMF solution of the crosslinker MHA-DIB (25 wt %, 1.8 g) were dropwise added with stirring. This system was heated to 60° C. in an oil bath. Upon the addition of 0.15 g of APS, this mixture was poured into the oil phase and the accelerator TMEDA (0.40 mL dissolved in 2 mL mineral oil) was added immediately. About 30 min later, the beads thus obtained were purified in the way similar to that used in Example 5. This kind of beads in the buffer solution (pH=7.4) degraded completely within 1.5 days at 37° C. As shown in Table 4, by using different monomers and/or crosslinker, several kinds of copolymer beads were prepared.

Example 23

Temporary Embolization of Canine Renal Arteries

Background & Methods

This study assessed the occlusion and recanalization that can be obtained following temporary arterial embolization with degradable microspheres. Specifically, degradable polymeric microspheres of the present invention were assessed. The beads used were synthesized as in Example 12. Bead sizes used were 300 -500 micrometer; and the beads had a degradation time of approximately three weeks. The beads were stored in pH 2.5 buffer prior to embolization; immediately prior to embolization, the storage buffer was replaced with a solution buffered at physiological pH.

The occlusion obtained in canine renal arteries after percutaneous embolization with temporary particles was evaluated. Specifically, the evaluation focused on the effects of temporary polymer spheres on three dogs. Follow-up angiograms were performed on a weekly basis for a total of three weeks. One kidney was left intact in two of the dogs, and the controlateral renal artery was embolized with Embogold® particles in the third dog. At the time of sacrifice, one intact kidney in one dog was embolized with temporary spheres immediately before barbiturate overdose in an effort to document their appearance and pathology.

Results

Figure 2:
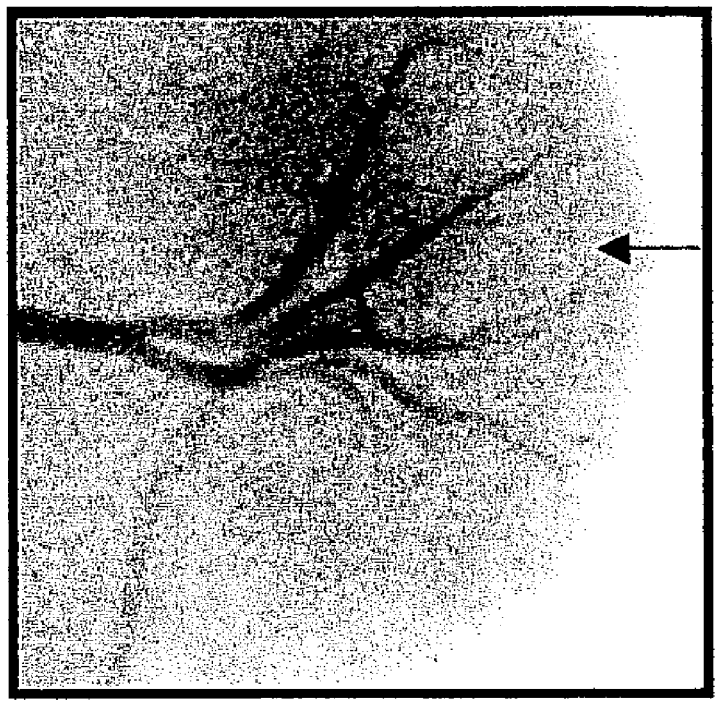
FIG. 2 depicts an angiogram of a kidney three weeks after embolization with degradable polymeric microspheres according to a method of the present invention; notably, one artery remained stenotic at three weeks. See Example 23.

All the dogs survived without adverse effects. Embolization in a supraselective fashion could be performed in all three animals. In all cases, arterial occlusions that persisted at one week were recanalized at three weeks, although the nephrographic defects caused by the occlusion caused a permanent infarction. See FIG. 1. Further, one artery remained stenotic at three weeks. See FIG. 2. The kidney embolized with permanent spheres did not show recanalization at three weeks.

Figure 3:
FIG. 3 depicts views of kidneys harvested from two animals that were embolized with degradable microspheres on one side only; the embolized kidneys are visibly distinct from the normal kidneys. See Example 23.
Figure 3:
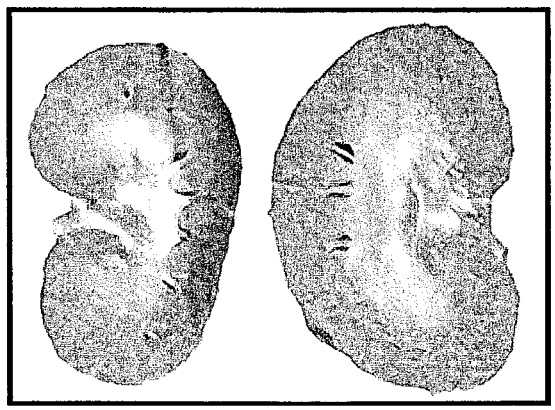
Figure 4:
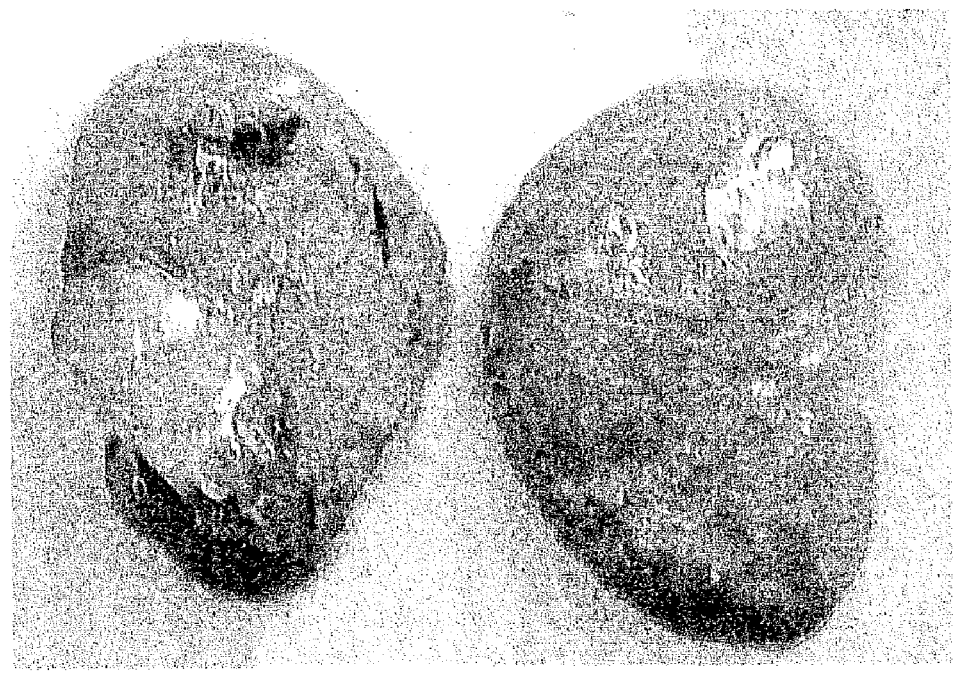
FIG. 4 depicts views of the kidneys harvested from an animal in which one kidney was embolized with permanent Embogold® microspheres; the embolized kidney is visibly distinct from the normal kidney. See Example 23.
Figure 4:
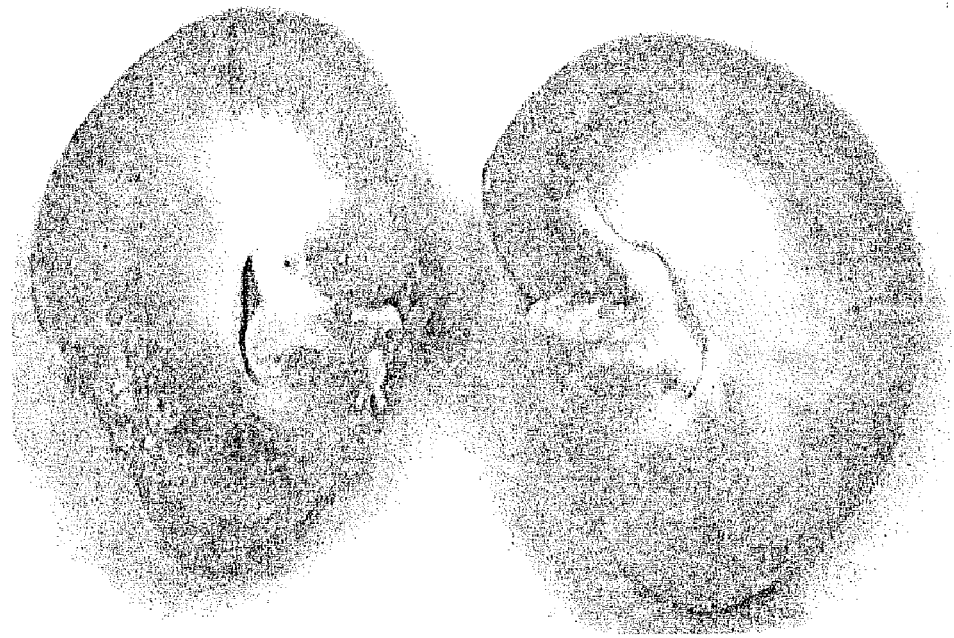

In two animals that were embolized with temporary spheres on one side only, the effects of embolization were evident as compared to normal kidneys. See FIG. 3. However, the effects were much less severe than those observed in the kidney embolized with Embogold® particles for comparison in one of these three animals. See FIG. 4. In all kidneys, the detected changes were typical of infarcts.

Figure 5:
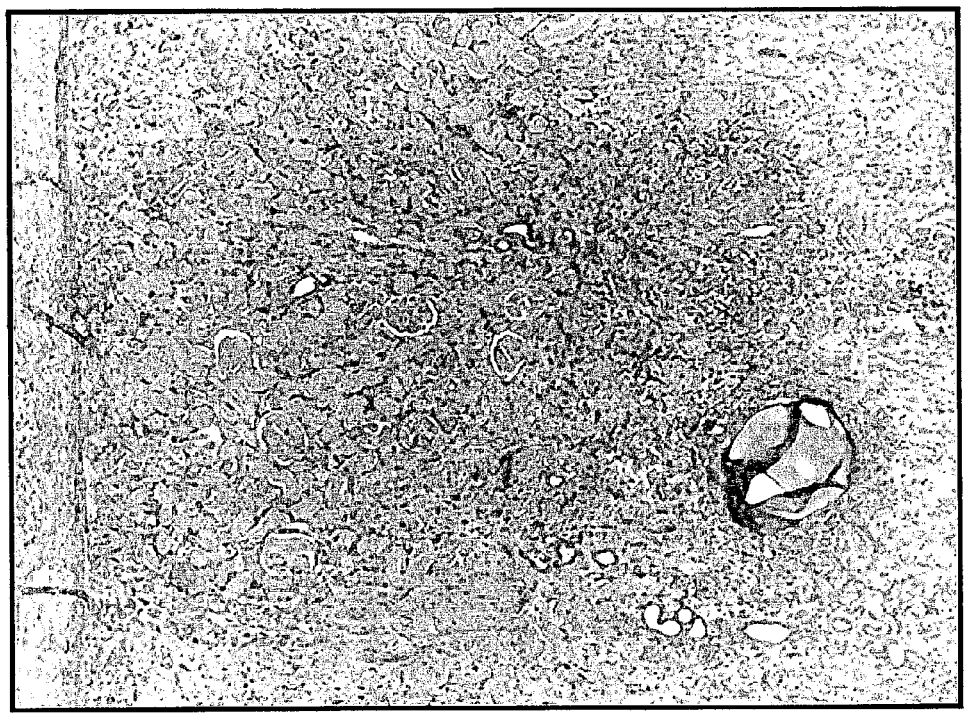
FIG. 5 depicts histological sections from kidneys embolized with permanent Embogold® microspheres showing extensive infarction; the microparticles tended to be close to the cortical surface of the organs, and were accompanied by a moderate inflammatory reaction. See Example 23.

Following sectioning and histopathological processing, all kidneys treated with Embogold® particles showed extensive infarction; further, the embolic particles were clearly visible. Moreover, the embolic particles tended to be close to the cortical surface of the organs, where they were accompanied by a moderate inflammatory reaction. See FIG. 5.

Figure 6:
FIG. 6 depicts histological sections from kidneys embolized with degradable microspheres revealing cortical infarctions; microparticles in various stages of degradation and phagocytosis are visible. See Example 23.

In the kidneys embolized with degradable microspheres, cortical infarctions could also be found. Microparticles, sometimes intact but encapsulated, but most often in various stages of degradation and phagocytosis, could also be detected. See FIG. 6. In certain locations, only the remaining inflammatory reaction and arterial neointima thickening could be observed as a witness to the previous presence of these degradable microparticles.

Discussion

In this animal model, it is difficult to determine immediately after embolization where the embolic microparticles will actually lodge. By comparison of the results with those obtained using permanent microspheres, it is concluded that embolized arteries recanalized, although the effect of even a temporary occlusion was an infarct. At the time of autopsy, i.e., at three weeks, some of the degradable microspheres were still present at various stages of degradation. Importantly, the degradable, polymeric microspheres achieved the goal of temporary occlusion for up to three weeks.

In sum, the degradable embolic microparticles caused less infarction than Embogold® particles. Although angiographic changes resulting from the embolization had disappeared at three weeks, a protion of the degradable embolic microparticles at various stages of degradation were still present at pathology at three weeks. The degradable embolic microspheres caused transient occlusions, i.e., for three weeks.

Incorporation By Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of embolizing a vascular site in a mammal, comprising the step of:

introducing into the vasculature of a mammal a microparticle comprising a hydrolytically degradable crosslinked hydrogel, thereby embolizing a vascular site of said mammal; wherein said hydrolytically degradable crosslinked hydrogel comprises a crosslink derived from a compound selected from the group consisting of a compound of formula 1 and a compound of formula 2; the compound of formula 1 is represented by:

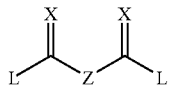

wherein

X represents independently for each occurrence O or S;

L represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents (CR$_2$)$_n$, (CR$_2$)$_n$J(CR$_2$)$_m$, or (CR$_2$)$_n$Ar(CR$_2$)$_m$;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

n represents independently for each occurrence an integer in the range 1-10; and m represents independently for each occurrence an integer in the range 0-10; and the compound of formula 2 is represented by:

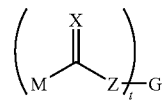

wherein

X represents independently for each occurrence O or S;

M represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents (CR$_2$)$_n$, (CR$_2$)$_n$J(CR$_2$)$_m$, or (CR$_2$)$_n$Ar(CR$_2$)$_m$;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

G represents (CR$_{(4-t)}$), aryl, or heteroaryl;

n represents independently for each occurrence an integer in the range 1-10; and t represents 3 or 4.

2. The method of claim 1, wherein said hydrolytically degradable crosslinked hydrogel comprises a crosslink that substantially hydrolyzes only at about physiological pH.

3. The method of claim 1, wherein said hydrolytically degradable crosslinked hydrogel comprises a crosslink that does not substantially hydrolyze at a pH below about 5.

4. The method of claim 1, wherein said hydrolytically degradable crosslinked hydrogel comprises an acrylic acid, acrylate, or acrylamide.

5. The method of claim 1, wherein said hydrolytically degradable crosslinked hydrogel comprises acrylic acid, 2-hydroxyethyl acrylate, oligo(ethylene glycol) 2-methacrylate, acrylamide, N,N-dimethylacrylamide, or N-(tris(hydroxymethyl)methyl)acrylamide.

6. The method of claim 1, wherein said hydrolytically degradable crosslinked hydrogel comprises a first acrylamide and a second acrylamide.

7. The method of claim 1, wherein said hydrolytically degradable crosslinked hydrogel comprises a first acrylamide and a second acrylamide, wherein said first acrylamide is acrylamide or N,N-dimethylacrylamide.

8. The method of claim 1, wherein said hydrolytically degradable crosslinked hydrogel comprises a first acrylamide and a second acrylamide, wherein said second acrylamide is N-(tris(hydroxymethyl)methyl)acrylamide.

9. The method of claim 1, wherein said hydrolytically degradable crosslinked hydrogel comprises a first acrylamide and a second acrylamide, wherein said first acrylamide is acrylamide or N,N-dimethylacrylamide; and said second acrylamide is N-(tris(hydroxymethyl)methyl)acrylamide.

10. The method of claim 1, wherein said hydrolytically degradable crosslinked hydrogel comprises an acrylamide and an acrylate.

11. The method of claim 1, wherein said hydrolytically degradable crosslinked hydrogel comprises an acrylamide and an acrylate, wherein said acrylamide is acrylamide or N,N-dimethylacrylamide.

12. The method of claim 1, wherein said hydrolytically degradable crosslinked hydrogel comprises an acrylamide and an acrylate, wherein said acrylate is acrylic acid, 2-hydroxyethyl acrylate, or oligo(ethylene glycol) 2-methacrylate.

13. The method of claim 1, wherein said hydrolytically degradable crosslinked hydrogel comprises an acrylamide and an acrylate, wherein said acrylamide is acrylamide or N,N-dimethylacrylamide; and said acrylate is acrylic acid, 2-hydroxyethyl acrylate, or oligo(ethylene glycol) 2-methacrylate.

14. The method of claim 1, wherein said hydrolytically degradable crosslinked hydrogel comprises a first acrylate and a second acrylate.

15. The method of claim 1, wherein said hydrolytically degradable crosslinked hydrogel comprises a first acrylate and a second acrylate, wherein said first acrylate is acrylic acid, 2-hydroxyethyl acrylate, or oligo(ethylene glycol) 2-methacrylate.

16. The method of claim 1, wherein said hydrolytically degradable crosslinked hydrogel comprises a first acrylate and a second acrylate, wherein said first acrylate is acrylic acid, 2-hydroxyethyl acrylate, or oligo(ethylene glycol) 2-methacrylate; and said second acrylate is acrylic acid, 2-hydroxyethyl acrylate, or oligo(ethylene glycol) 2-methacrylate.

17. The method of claim 1, wherein said hydrolytically degradable crosslinked hydrogel comprises a crosslink derived from a compound of formula 1; and X represents O.

18. The method of claim 1, wherein said hydrolytically degradable crosslinked hydrogel comprises a crosslink derived from a compound of formula 1; and L represents —NH—O-Q.

19. The method of claim 1, wherein said hydrolytically degradable crosslinked hydrogel comprises a crosslink derived from a compound of formula 1; and Q represents acryloyl, or 2-methacryloyl.

20. The method of claim 1, wherein said hydrolytically degradable crosslinked hydrogel comprises a crosslink derived from a compound of formula 1; and R represents H.

21. The method of claim 1, wherein said hydrolytically degradable crosslinked hydrogel comprises a crosslink derived from a compound of formula 1; and Z represents $(CR_2)_n$.

22. The method of claim 1, wherein said hydrolytically degradable crosslinked hydrogel comprises a crosslink derived from a compound of formula 1; X represents O; and L represents —NH—O-Q.

23. The method of claim 1, wherein said hydrolytically degradable crosslinked hydrogel comprises a crosslink derived from a compound of formula 1; X represents O; L represents —NH—O-Q; and Q represents acryloyl, or 2-methacryloyl.

24. The method of claim 1, wherein said hydrolytically degradable crosslinked hydrogel comprises a crosslink derived from a compound of formula 1; X represents O; L represents —NH—O-Q; Q represents acryloyl, or 2-methacryloyl; and R represents H.

25. The method of claim 1, wherein said hydrolytically degradable crosslinked hydrogel comprises a crosslink derived from a compound of formula 1; X represents O; L represents —NH—O-Q; Q represents acryloyl, or 2-methacryloyl; R represents H; and Z represents $(CR_2)_n$.

26. The method of claim 1, wherein said hydrolytically degradable crosslinked hydrogel comprises a crosslink derived from a compound of formula 2; and X represents O.

27. The method of claim 1, wherein said hydrolytically degradable crosslinked hydrogel comprises a crosslink derived from a compound of formula 2; and M represents —NH—O-Q.

28. The method of claim 1, wherein said hydrolytically degradable crosslinked hydrogel comprises a crosslink derived from a compound of formula 2; and Q represents acryloyl, or 2-methacryloyl.

29. The method of claim 1, wherein said hydrolytically degradable crosslinked hydrogel comprises a crosslink derived from a compound of formula 2; and R represents H.

30. The method of claim 1, wherein said hydrolytically degradable crosslinked hydrogel comprises a crosslink derived from a compound of formula 2; X represents O; and M represents —NH—O-Q.

31. The method of claim 1, wherein said hydrolytically degradable crosslinked hydrogel comprises a crosslink derived from a compound of formula 2; X represents O; M represents —NH—O-Q; and Q represents acryloyl, or 2-methacryloyl.

32. The method of claim 1, wherein said hydrolytically degradable crosslinked hydrogel comprises a crosslink derived from a compound of formula 2; X represents O; M represents —NH—O-Q; Q represents acryloyl, or 2-methacryloyl; and R represents H.

33. A method of embolizing a vascular site in a mammal, comprising the step of:

introducing into the vasculature of a mammal a microparticle comprising a hydrolytically degradable crosslinked hydrogel, thereby embolizing a vascular site of said mammal; wherein said hydrolytically degradable crosslinked hydrogel comprises a crosslink derived from a compound selected from the group consisting of a compound of formula 1 and a compound of formula 2; the compound of formula 1 is represented by:

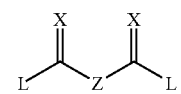

wherein
X represents independently for each occurrence O or S;
L represents independently for each occurrence —O—NH-Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_nC(O)$—, 2-alkylacryloylO$(CR_2)_nC(O)$—, 3-alkylacryloylO$(CR_2)_nC(O)$—, 2,3-dialkylacryloylO$(CR_2)_nC(O)$—, 3,3-dialkylacryloylO$(CR_2)_nC(O)$—, 2,3,3-trialkylacryloylO$(CR_2)_nC(O)$—, (diene)C(O)—, (vinyl)$(CR_2)_nC(O)$—, or (vinyl)ArC(O)—;
R represents independently for each occurrence H or alkyl;
Z represents —$NH(CR_2)_nNH$—, or —$NH(CR_2)_nJ(CR_2)_mNH$—;
Ar represents independently for each occurrence aryl or heteroaryl;
J represents independently for each occurrence O, S, NR, cycloalkyl, heterocyclyl, $(CH_2CH_2O)_n$, or $(CH_2CH_2N(R))_n$;
n represents independently for each occurrence an integer in the range 1-10; and
m represents independently for each occurrence an integer in the range 0-10; and the compound of formula 2 is represented by:

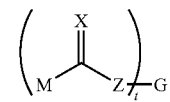

wherein
X represents independently for each occurrence O or S;
M represents independently for each occurrence —O—NH-Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_nC(O)$—, 2-alkylacryloylO$(CR_2)_nC(O)$—, 3-alkylacryloylO$(CR_2)_nC(O)$—, 2,3-dialkylacryloylO$(CR_2)_nC(O)$—, 3,3-dialkylacryloylO$(CR_2)_nC(O)$—, 2,3,3-trialkylacryloylO$(CR_2)_nC(O)$—, (diene)C(O)—, (vinyl)$(CR_2)_nC(O)$—, or (vinyl)ArC(O)—;

R represents independently for each occurrence H or alkyl;

Z represents —$NH(CR_2)_nNH$—, or —$NH(CR_2)_nJ(CR_2)_mNH$—;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

G represents $(CR_{(4-t)})$, aryl, or heteroaryl;

n represents independently for each occurrence an integer in the range 1-10;

m represents independently for each occurrence an integer in the range 0-10; and t represents 3 or 4.

34. The method of claim 33, wherein said hydrolytically degradable crosslinked hydrogel comprises a crosslink derived from a compound of formula 1; and X represents O.

35. The method of claim 33, wherein said hydrolytically degradable crosslinked hydrogel comprises a crosslink derived from a compound of formula 1; and Q represents acryloyl, or 2-methacryloyl.

36. The method of claim 33, wherein said hydrolytically degradable crosslinked hydrogel comprises a crosslink derived from a compound of formula 1; and R represents H.

37. The method of claim 33, wherein said hydrolytically degradable crosslinked hydrogel comprises a crosslink derived from a compound of formula 1; and Z represents —$NH(CR_2)_nNH$—.

38. The method of claim 33, wherein said hydrolytically degradable crosslinked hydrogel comprises a crosslink derived from a compound of formula 1; X represents O; L represents —O—NH-Q; and Q represents acryloyl, or 2-methacryloyl.

39. The method of claim 33, wherein said hydrolytically degradable crosslinked hydrogel comprises a crosslink derived from a compound of formula 1; X represents O; L represents —O—NH-Q; Q represents acryloyl, or 2-methacryloyl; and R represents H.

40. The method of claim 33, wherein said hydrolytically degradable crosslinked hydrogel comprises a crosslink derived from a compound of formula 1; X represents O; L represents —O—NH-Q; Q represents acryloyl, or 2-methacryloyl; R represents H; and Z represents —$NH(CR_2)_nNH$—.

41. The method of claim 33, wherein said hydrolytically degradable crosslinked hydrogel comprises a crosslink derived from a compound of formula 2; and X represents O.

42. The method of claim 33, wherein said hydrolytically degradable crosslinked hydrogel comprises a crosslink derived from a compound of formula 2; and Q represents acryloyl, or 2-methacryloyl.

43. The method of claim 33, wherein said hydrolytically degradable crosslinked hydrogel comprises a crosslink derived from a compound of formula 2; and R represents H.

44. The method of claim 33, wherein said hydrolytically degradable crosslinked hydrogel comprises a crosslink derived from a compound of formula 2; X represents O; M represents —O—NH-Q; and Q represents acryloyl, or 2-methacryloyl.

45. The method of claim 33, wherein said hydrolytically degradable crosslinked hydrogel comprises a crosslink derived from a compound of formula 2; X represents O; M represents —O—NH-Q; Q represents acryloyl, or 2-methacryloyl; and R represents H.

46. The method of claim 1 or 33, wherein said vascular site is proximal to a hemorrhage, cancerous tissue, a uterine fibroid, a tumor, or an organ.

47. The method of claim 1 or 33, wherein said hydrolytically degradable crosslinked hydrogel embolizes said vascular site for less than about three months.

48. The method of claim 1 or 33, wherein said hydrolytically degradable crosslinked hydrogel embolizes said vascular site for less than about two months.

49. The method of claim 1 or 33, wherein said hydrolytically degradable crosslinked hydrogel embolizes said vascular site for less than about one month.

50. The method of claim 1 or 33, wherein said hydrolytically degradable crosslinked hydrogel embolizes said vascular site for less than about fourteen days.

51. The method of claim 1 or 33, wherein said hydrolytically degradable crosslinked hydrogel embolizes said vascular site for less than about seven days.

52. The method of claim 1 or 33, wherein said hydrolytically degradable crosslinked hydrogel embolizes said vascular site for less than about three days.

53. The method of claim 1 or 33, wherein said hydrolytically degradable crosslinked hydrogel embolizes said vascular site for less than about one day.

54. The method of claim 1 or 33, wherein said microparticle further comprises a contrast-enhancing agent.

55. The method of claim 54, wherein said contrast-enhancing agent is selected from the group consisting of radiopaque materials, paramagnetic materials, heavy atoms, transition metals, lanthanides, actinides, dyes, and radionuclide-containing materials.

56. The method of claim 1 or 33, wherein said microparticle further comprises a biologically active agent.

57. The method of claim 1 or 33, wherein said mammal is a primate, equine, canine or feline.

58. The method of claim 1 or 33, wherein said mammal is a human.

59. The method of claim 1 or 33, wherein said microparticle is introduced into the vasculature of said mammal using a catheter.

60. The method of claim 1 or 33, wherein said microparticle is a sphere, rod, plug, or coil.

61. The method of claim 1 or 33, wherein said microparticle is a sphere.

62. The method of claim 61, wherein the spherical microparticle has a diameter in the range of 10-5,000 μm inclusive.

63. The method of claim 61, wherein the spherical microparticle has a diameter in the range of 40-3,000 μm inclusive.

* * * * *